(12) United States Patent
Nakhla

(10) Patent No.: US 11,918,673 B2
(45) Date of Patent: Mar. 5, 2024

(54) SKIN CARE PRODUCT WITH PROTEIN MATRIX

(71) Applicant: Eighth Day Labs, LLC, Santa Ana, CA (US)

(72) Inventor: Tony Nakhla, Santa Ana, CA (US)

(73) Assignee: Eighth Day Labs, LLC, Santa Ana, CA (US)

( * ) Notice: Subject to any disclaimer, the term of this patent is extended or adjusted under 35 U.S.C. 154(b) by 98 days.

(21) Appl. No.: 17/323,421

(22) Filed: May 18, 2021

(65) Prior Publication Data

US 2021/0361553 A1 Nov. 25, 2021

Related U.S. Application Data

(60) Provisional application No. 63/026,781, filed on May 19, 2020.

(51) Int. Cl.

| | |
|---|---|
| *A61K 8/64* | (2006.01) |
| *A61K 8/44* | (2006.01) |
| *A61K 8/49* | (2006.01) |
| *A61K 8/73* | (2006.01) |
| *A61Q 19/00* | (2006.01) |
| *A61Q 19/02* | (2006.01) |
| *A61Q 19/08* | (2006.01) |

(52) U.S. Cl.
CPC ............ *A61K 8/64* (2013.01); *A61K 8/44* (2013.01); *A61K 8/447* (2013.01); *A61K 8/4913* (2013.01); *A61K 8/4946* (2013.01); *A61K 8/735* (2013.01); *A61Q 19/00* (2013.01); *A61Q 19/02* (2013.01); *A61Q 19/08* (2013.01)

(58) Field of Classification Search
CPC . A61K 8/64; A61K 8/44; A61K 8/447; A61K 8/4913; A61K 8/4946; A61K 8/735; A61Q 19/00; A61Q 19/02; A61Q 19/08
See application file for complete search history.

(56) References Cited

U.S. PATENT DOCUMENTS

| | | | | |
|---|---|---|---|---|
| 2009/0186805 A1* | 7/2009 | Tabor | .................. | A61K 48/005 |
| | | | | 435/459 |
| 2016/0367676 A1* | 12/2016 | Burnam | .................. | A61P 43/00 |

OTHER PUBLICATIONS

LABIO, Co., "BIO-Placenta," from https://www.ulprospector.com/en/na/PersonalCare/Detail/30848/637882/BIO-Placenta, pp. 1-2. Accessed Feb. 16, 2023. (Year: 2023).*
PCT International Search Report and Written Opinion from the International Application, PCT/US/2021/032921, dated Aug. 13, 2021, 13 pages.
"Bio-Placenta Pseudo Placenta con azione anti-aging," Gale & COSM, s.r.l., Cosmetic Technology | Luglio-Agosoto 2016(19)4, pp. 62-64, Retrieved from the Internet: URL:http://galecosm.com/home/wp-content/uploads/2016/09/BIOPLACENTA_CEC-2016.pdf.
"Ageless Real Eye Cream for Face", MINTEL, Jan. 1, 2020, 3 pages.
Real Eye Cream for Face Special Day, Apr. 7, 2017, MINTEL, 6 pages.
"BIO-Placenta Analogous placenta with synergic effects and safety," Independent Chemical Corporation, 2 pages, Retrieved from European Patent Center date mailed Feb. 28, 2023, Cited in corresponding PCT Application No. PCT/US2021/032921.

* cited by examiner

*Primary Examiner* — Julie Ha
(74) *Attorney, Agent, or Firm* — Tucker Ellis LLP; Michael G. Craig

(57) ABSTRACT

One or more techniques and/or systems are disclosed for formulating a skin care product to mitigate aging or to restore damaged skin. One skin care product includes a blend of growth factors, peptides, and amino acids. Also disclosed is a skin care product formed from a synthesized protein matrix. The synthesized protein matrix can mimic the regenerative effects of human placental proteins, which are desirable when applied to skin because, as skin loses its regenerative properties, humans shows signs of aging, and a decrease in healing capabilities. The exemplary skin-care products disclosed herein can be applied to skin to help mitigate this skin aging process or to restore damaged skin.

12 Claims, 29 Drawing Sheets

| Questionnaire Response Summary – 4 Weeks | | |
|---|---|---|
| | Strongly Agree to Slightly Agree | Disagree or Strongly Disagree |
| The regenerative serum helps to smooth my fine lines and wrinkles. | 100% | 0% |
| My fine lines and wrinkles are smoother after using the regenerative serum. | 100% | 0% |
| My skin showed significant improvement in fine lines and wrinkles. | 97% | 3% |
| The regenerative serum helps to reduce the size of my pores. | 97% | 3% |
| My pore size is smaller after using the regenerative serum. | 93% | 7% |
| My pores were significantly decreased in size. | 93% | 7% |
| The regenerative serum helped my skin look brighter. | 97% | 3% |
| My skin appeared less dull after using the regenerative serum. | 100% | 0% |
| My skin appeared brighter after using the regenerative serum. | 93% | 7% |
| This regenerative serum gave my skin an instant glow. | 97% | 3% |
| My skin appeared more radiant after using the regenerative serum. | 97% | 3% |
| My skin appeared radiant and glowing after using the regenerative serum. | 97% | 3% |
| The regenerative serum helped give the appearance of being plumped and hydrated. | 97% | 3% |
| My skin appeared more plump after using the regenerative serum. | 90% | 10% |
| My skin appeared after using the regenerative serum. | 97% | 3% |
| The regenerative serum helped my skin appear firm and tight. | 100% | 0% |
| My skin appeared more firm and tight after using the regenerative serum. | 100% | 0% |
| My skin appeared firmer after using the regenerative serum. | 97% | 3% |
| The regenerative serum helped even out my skin tone. | 90% | 10% |
| My skin appeared more even after using the regenerative serum. | 97% | 3% |
| My skin tone appeared even after using the regenerative serum. | 97% | 3% |
| The regenerative serum helped diminish the appearance of sun damage and environmental stressors. | 87% | 13% |
| My skin appeared to have less sun damage after using the regenerative serum. | 83% | 17% |
| My skin was showed signs of less sun damage and environmental stressors after using the regenerative serum. | 83% | 17% |
| The regenerative serum helped give the appearance of having less redness in my skin. | 97% | 3% |
| My skin appeared less red after using the regenerative serum. | 90% | 10% |
| My skin was much less red after using the regenerative serum. | 90% | 10% |

FIG. 5

| Subject No. | Initials | Age | Sex | Race | Subject No. | Initials | Age | Sex | Race |
|---|---|---|---|---|---|---|---|---|---|
| 1 | GHA | 65 | F | WH | 17 | E-F | 37 | F | WH |
| 2 | P-S | 36 | F | HS | 18 | RLD | 37 | F | WH |
| 3 | AMH | 49 | F | BA | 19 | R-A | 41 | F | WH |
| 4 | C-L | 38 | F | WH | 20 | GMS | 55 | F | WH |
| 5 | DEC | 37 | F | HS | 21 | DMC | 44 | F | WH |
| 6 | Y-C | 35 | F | HS | 22 | BSS | 39 | F | HS |
| 7 | MDG | 37 | F | HS | 23 | P-C | 36 | F | HS |
| 8 | J-A | 59 | F | WH | 24 | J-S | 40 | F | WH |
| 9 | SEA | 59 | F | HS | 25 | D-G | 38 | F | HS |
| 10 | SMB | 38 | F | WH | 26 | J-K | 43 | F | WH |
| 11 | NAG | 48 | F | HS | 27 | M-C | 46 | F | HS |
| 12 | CAC | 42 | F | BA | 28 | CAC | 38 | F | HS |
| 13 | S-C | 38 | F | BA | 29 | S-C | 37 | F | HS |
| 14 | E-G | 48 | F | HS | 30 | K-A | 45 | F | HS |
| 15 | RCA | 57 | F | WH | 31 | S-V | 45 | F | HS |
| 16 | B-C | 43 | F | HS | | | | | |

BA = Black
HS = Hispanic/Latino
WH = White

Shaded area = Discontinued subject

FIG. 6

CUTOMETER® MEASUREMENTS - R0 PARAMETER

Test Article: Eighth Day Regenerative Serum

| SUBJECT NO | BASELINE | WEEK 4 |
|---|---|---|
| 1 | 0.292 | 0.196 |
| 2 | 0.278 | 0.174 |
| 3 | 0.290 | 0.120 |
| 4 | 0.257 | 0.114 |
| 5 | 0.207 | 0.114 |
| 6 | 0.242 | 0.123 |
| 7 | 0.203 | 0.119 |
| 8 | 0.209 | 0.120 |
| 9 | 0.240 | 0.113 |
| 10 | 0.232 | 0.078 |
| 11 | 0.278 | 0.113 |
| 12 | 0.259 | 0.181 |
| 13 | 0.284 | 0.181 |
| 14 | 0.311 | 0.142 |
| 15 | 0.324 | 0.179 |
| 16 | 0.271 | 0.170 |
| 17 | 0.259 | 0.181 |
| 18 | 0.238 | 0.175 |
| 19 | 0.260 | 0.181 |
| 20 | 0.275 | 0.160 |
| 21 | 0.280 | 0.113 |
| 22 | 0.244 | 0.179 |
| 23 | 0.333 | 0.178 |
| 24 | Discontinued | |
| 25 | 0.278 | 0.158 |
| 26 | 0.264 | 0.117 |
| 27 | 0.259 | 0.097 |
| 28 | 0.225 | 0.148 |
| 29 | 0.236 | 0.134 |
| 30 | 0.259 | 0.178 |
| 31 | 0.249 | 0.123 |
| MEAN | 0.261 | 0.145 |

FIG. 7

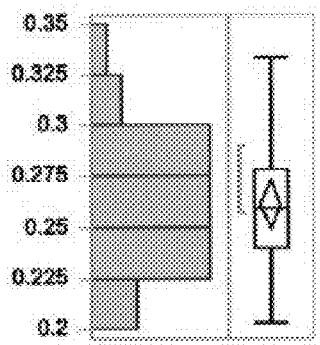

Descriptive Statistics Baseline

Distributions

Quantiles

| | | |
|---|---|---|
| 100.0% | maximum | 0.333 |
| 99.5% | | 0.333 |
| 97.5% | | 0.333 |
| 90.0% | | 0.3091 |
| 75.0% | quartile | 0.2785 |
| 50.0% | median | 0.259 |
| 25.0% | quartile | 0.2395 |
| 10.0% | | 0.2106 |
| 2.5% | | 0.203 |
| 0.5% | | 0.203 |
| 0.0% | minimum | 0.203 |

Summary Statistics

| | |
|---|---|
| Mean | 0.2612 |
| Std Dev | 0.0316548 |
| Std Err Mean | 0.0057794 |
| Upper 95% Mean | 0.2730201 |
| Lower 95% Mean | 0.2493799 |
| N | 30 |

FIG. 8

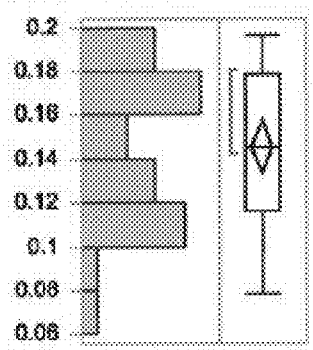

Descriptive Statistics 4 Weeks

Distributions

Quantiles

| | | |
|---|---|---|
| 100.0% | maximum | 0.196 |
| 99.5% | | 0.196 |
| 97.5% | | 0.196 |
| 90.0% | | 0.181 |
| 75.0% | quartile | 0.17825 |
| 50.0% | median | 0.145 |
| 25.0% | quartile | 0.11625 |
| 10.0% | | 0.113 |
| 2.5% | | 0.078 |
| 0.5% | | 0.078 |
| 0.0% | minimum | 0.078 |

Summary Statistics

| | |
|---|---|
| Mean | 0.1453 |
| Std Dev | 0.0325027 |
| Std Err Mean | 0.0059342 |
| Upper 95% Mean | 0.1574367 |
| Lower 95% Mean | 0.1331633 |
| N | 30 |

FIG. 9

CUTOMETER® MEASUREMENTS - R2 PARAMETER

Test Article: Eighth Day Regenerative Serum

| SUBJECT NO | BASELINE | WEEK 4 |
|---|---|---|
| 1 | 0.452 | 0.597 |
| 2 | 0.540 | 0.523 |
| 3 | 0.514 | 0.558 |
| 4 | 0.518 | 0.544 |
| 5 | 0.358 | 0.544 |
| 6 | 0.591 | 0.610 |
| 7 | 0.434 | 0.471 |
| 8 | 0.512 | 0.558 |
| 9 | 0.383 | 0.434 |
| 10 | 0.466 | 0.500 |
| 11 | 0.385 | 0.434 |
| 12 | 0.483 | 0.553 |
| 13 | 0.504 | 0.553 |
| 14 | 0.351 | 0.361 |
| 15 | 0.509 | 0.570 |
| 16 | 0.565 | 0.606 |
| 17 | 0.541 | 0.553 |
| 18 | 0.395 | 0.457 |
| 19 | 0.465 | 0.553 |
| 20 | 0.458 | 0.594 |
| 21 | 0.414 | 0.434 |
| 22 | 0.484 | 0.570 |
| 23 | 0.511 | 0.562 |
| 24 | Discontinued | |
| 25 | 0.385 | 0.449 |
| 26 | 0.527 | 0.564 |
| 27 | 0.371 | 0.433 |
| 28 | 0.591 | 0.601 |
| 29 | 0.381 | 0.418 |
| 30 | 0.483 | 0.562 |
| 31 | 0.514 | 0.610 |
| MEAN | 0.470 | 0.526 |

SKIN CARE PRODUCT WITH PROTEIN MATRIX

CROSS-REFERENCE TO RELATED APPLICATIONS

This application claims priority to U.S. Ser. No. 63/026,781, entitled SKINCARE PRODUCT WITH PLACENTAL PROTEINS, filed May 19, 2020, which is incorporated herein by reference.

BACKGROUND

Human skin can lose its regenerative properties and begin to show signs of aging and a decrease in healing capabilities as a person ages. This change can happen due to an abundance of molecular reactions occurring at the cellular level. The result can be a lack of skin-elasticity that causes wrinkles and/or severe scarring after trauma. Often, people use skin care products on their skin to help reduce this typical aging process, and/or in an attempt to reverse the signs of aging skin.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques and systems described herein can be utilized to produce a skin care product comprising an exemplary skin care blend. The skin care blend can have desirable characteristics that may mitigate signs of aging or regenerate damaged skin. In one example, a skin care product comprising a synthesized protein matrix, that mimics the regenerative properties of placental proteins, can be produced. In this example, the skin care product can be applied to skin to help mitigate the skin's natural aging process or to heal damaged skin. The synthesized protein matrix can have certain desirable regenerative characteristics similar to those found in human placental proteins.

In one implementation, a skin care blend comprises a synthesized protein matrix, comprising sh-oligopeptide-2, sh-polypeptide-1, sh-polypeptide-9, sh-polypeptide-11, and sh-oligopeptide-1, a group of peptides, comprising acetyl hexapeptide-8, palmitoyl tripeptide-5, and palmitoyl tetrapeptide-7, and a group of amino acids, comprising acetyl glutamine, sodium hyaluronate, lysine HCL, alanine, histidine HCL, arginine, serine, proline, glutamic acid, threonine, valine, leucine, glycine, isoleucine, phenylalanine, taurine.

In another implementation, the synthesized protein matrix is generated from microbial bio-fermentation.

In another implementation, a skin care product comprises the skin care blend recited above, and glycerin, *Hedychium coronarium* root extract, tripeptide-1, *Polygonum aviculare* extract, honey, nonapeptide-1, acetyl heptapeptide-4, phytosphingosine, sea whip extract, niacinamide, hydrolyzed hyaluronic acid, aminobutyric acid, adenosine, thioctic acid, glycolic acid, folic acid ferment extract, polysorbate 20, allantoin, caprylyl glycol, lecithin, butylene glycol, 1,2-hexanediol, dextran, phenoxyethanol, ethylhexylglycerin, and xanthan gum.

In another implementation, the skin care product further comprises water and pentylene glycol.

In another implementation, the skin care product is a face serum.

In another implementation, the skin care product is configured to be applied to a user's face in the morning and in the evening to obtain a desired result.

In another implementation, the skin care product further comprises Manuka honey.

In an implementation, a skin care product comprises the skin care blend recited above, and water, ethylhexyl palmitate, *Butyrospermum parkii* butter, *Cocos nucifera* oil, cetearyl olivate, sorbitan oleate, stearyl alcohol, propanediol, glyceryl stearate, aloe barbadensis leaf juice, caprylhydroxamic acid, caprylyl glycol, glycerin, *alteromonas* ferment extract, glycosphingolipids, glycolipids, hydrolyzed hyaluronic acid, ferulic acid, retinyl palmitate, resveratrol, ergothioneine, *Linum usitatissimum* seed oil, *bacillus*/soybean/folic acid ferment extract, tocopherol, sodium PCA, 1,2-hexanediol, polysorbate 20, ethylhexylglycerin, allantoin, lecithin, butylene glycol, *Rosmarinus officinalis* leaf extract, *Lavandula agustifolia* oil, and xanthan gum.

In another implementation, the skin care product is moisturizer.

In another implementation, the skin care product is configured to be applied to a user's face in the morning and in the evening to obtain a desired result.

In an implementation, a skin care product comprises the skin care blend recited above, and water, zinc oxide, *Brassica napus* extract, dimethicone, cyclopentasiloxane, caprylic triglyceride, glycerin, propanediol, bentonite, cetearyl alcohol, montmorillonite, illite, sodium chloride, xanthan gum, citric acid, Manuka honey, polyglyceryl-8 oleate, polyhydroxystearic acid, dimethicone/vinyl dimethicone crosspolymer, lecithin, *bacillus*/folic acid/soybean ferment extract, caprylyl glycol, butylene glycol, 1,2-hexanediol, caprylyl glycol, allantoin, hyaluronic acid, dimethylmethoxy chromanyl palmitate, *Caesalpinia spinosa* fruit pod extract, *Helianthus annuus* sprout extract, maltodextrin, lactic acid, phenoxyethanol, ethylhexylglycerin In another implementation, the skin care product is a sun protection product.

In another implementation, the skin care product is configured to be applied to a user's face in the morning to obtain a desired result.

In an implementation, a skin care product comprises a synthesized protein matrix and a native protein matrix; wherein the synthesized protein matrix comprises epidermal growth factor, insulin-like growth factor-1, acidic fibroblast growth factor, basic fibroblast growth factor, vascular endothelial growth factor, vitamin B9, and acetyl glutamine.

In another implementation, the synthesized protein matrix is generated from microbial bio-fermentation.

In another implementation, the native protein matrix is synthesized from human tissue conditioned media.

In another implementation, the native protein matrix comprises human fibronectin, human collagen, human thrombospondin, human actin cytoplasmic, and human elastin.

In another implementation, the skin care product further comprises Manuka honey.

In another implementation, the skin care product further comprises shea butter, coconut oil, aloe, linseed oil, ergothioneine, vitamin A, vitamin C, vitamin E, resveratrol, coenzyme Q10, and ferulic acid.

In an implementation, a skin care product comprises a skin care blend, water, pentylene glycol, glycerin, *Hedychium coronarium* root extract, tripeptide-1, *Polygonum aviculare* extract, honey, nonapeptide-1, acetyl heptapeptide-4, phytosphingosine, sea whip extract, niacinamide, hydrolyzed hyaluronic acid, aminobutyric acid, adenosine, thioctic acid, glycolic acid, folic acid ferment extract, polysorbate 20, allantoin, caprylyl glycol, lecithin, butylene glycol, 1,2-hexanediol, dextran, phenoxyethanol, ethylhexylglycerin, and xanthan gum, wherein the skin care blend comprises a synthesized protein matrix, comprising sh-oligopeptide-2, sh-polypeptide-1, sh-polypeptide-9, sh-polypeptide-11, and sh-oligopeptide-1, a group of peptides, comprising acetyl hexapeptide-8, palmitoyl tripeptide-5, and palmitoyl tetrapeptide-7, a group of amino acids, comprising acetyl glutamine, sodium hyaluronate, lysine HCL, alanine, histidine HCL, arginine, serine, proline, glutamic acid, threonine, valine, leucine, glycine, isoleucine, phenylalanine, taurine. To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

FIG. 5 is chart illustrating an example result of the implementation of one or more techniques and/or one or more systems described herein.

FIG. 6 is chart illustrating an example result of the implementation of one or more techniques and/or one or more systems described herein.

FIG. 7 is chart illustrating an example result of the implementation of one or more techniques and/or one or more systems described herein.

FIG. 8 is chart illustrating an example result of the implementation of one or more techniques and/or one or more systems described herein.

FIG. 9 is chart illustrating an example result of the implementation of one or more techniques and/or one or more systems described herein.

FIG. 11 is chart illustrating an example result of the implementation of one or more techniques and/or one or more systems described herein.

Figure 12:
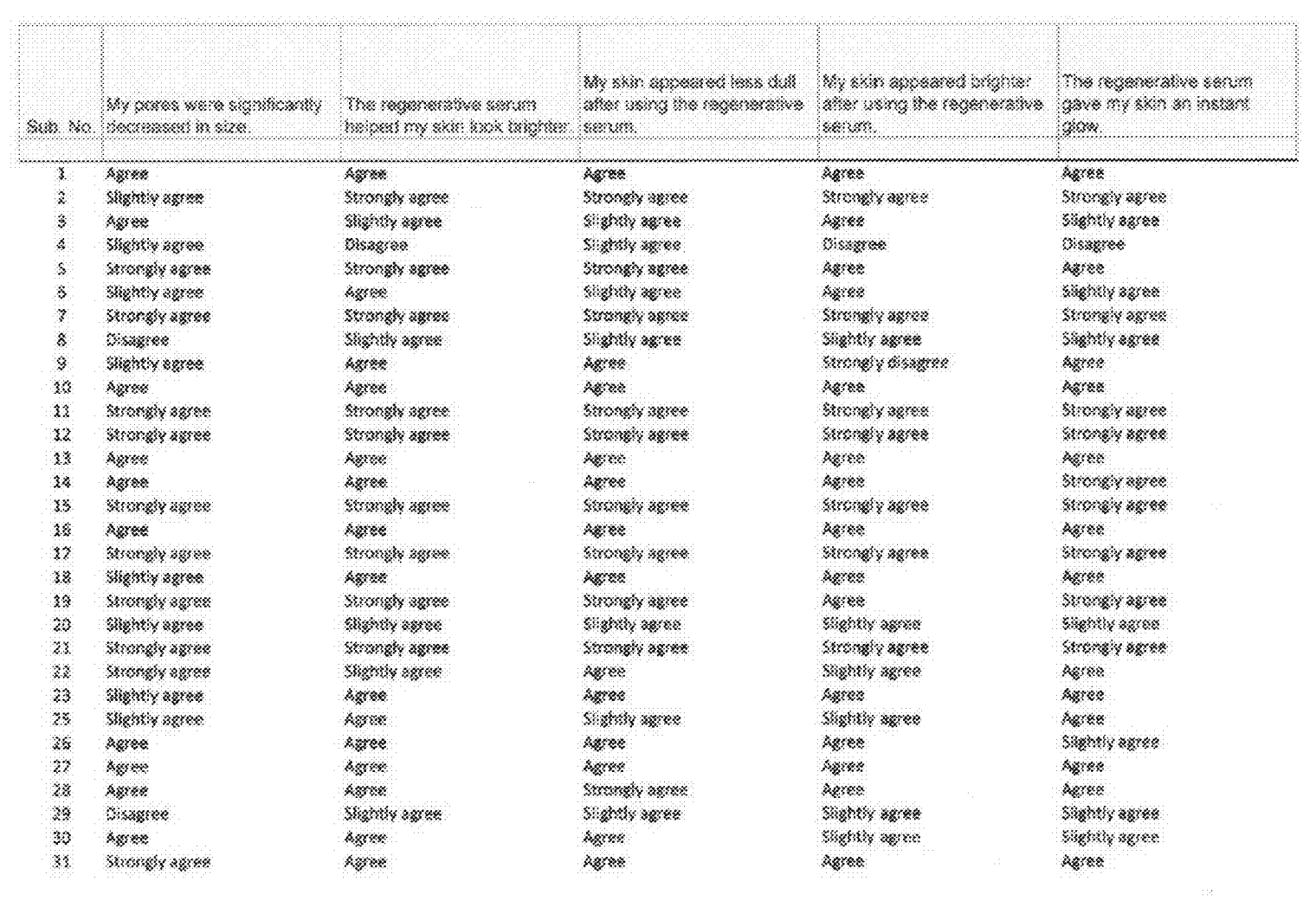

FIG. 12 is chart illustrating an example result of the implementation of one or more techniques and/or one or more systems described herein.

Figure 13:
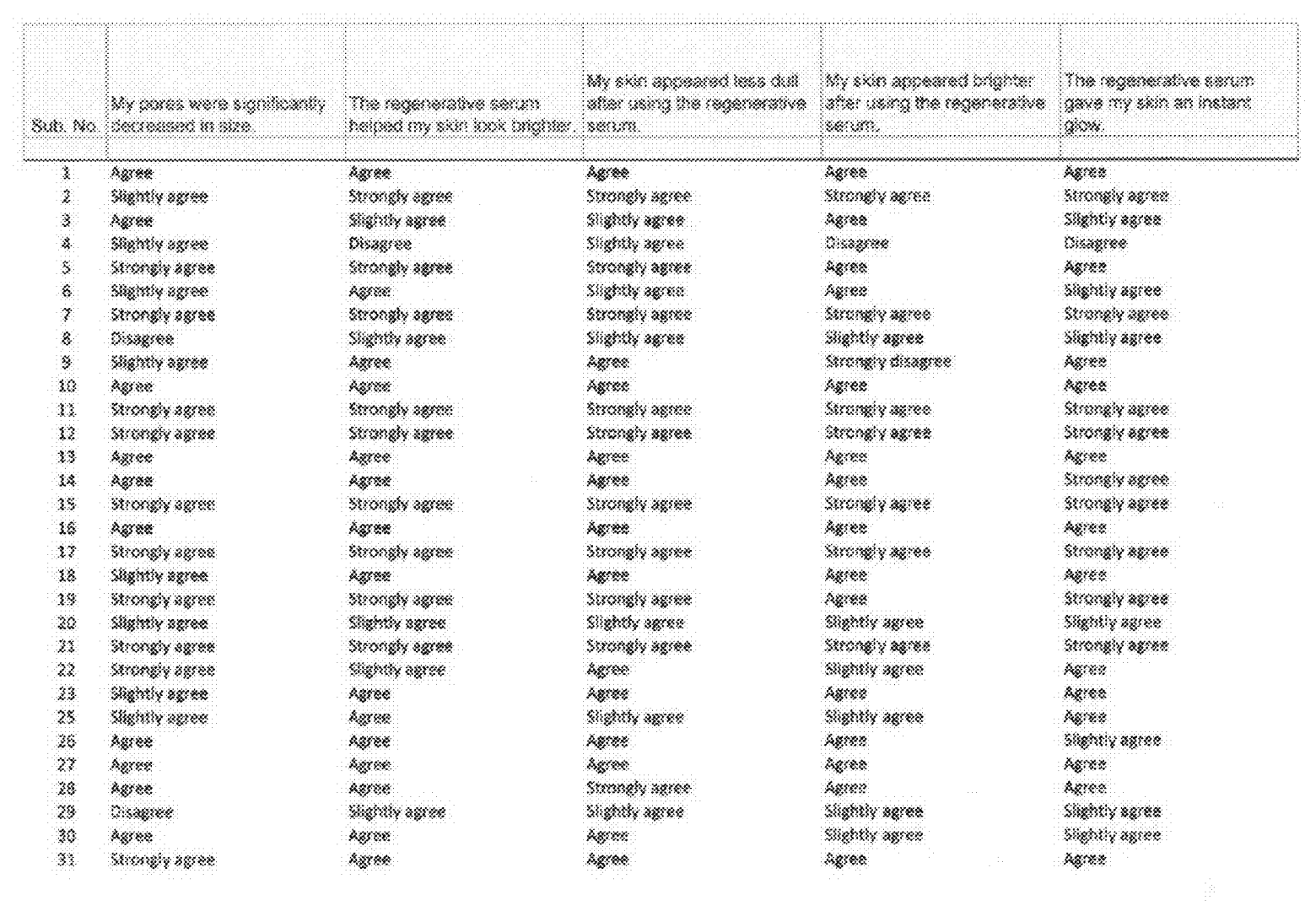

FIG. 13 is chart illustrating an example result of the implementation of one or more techniques and/or one or more systems described herein.

Figure 14:
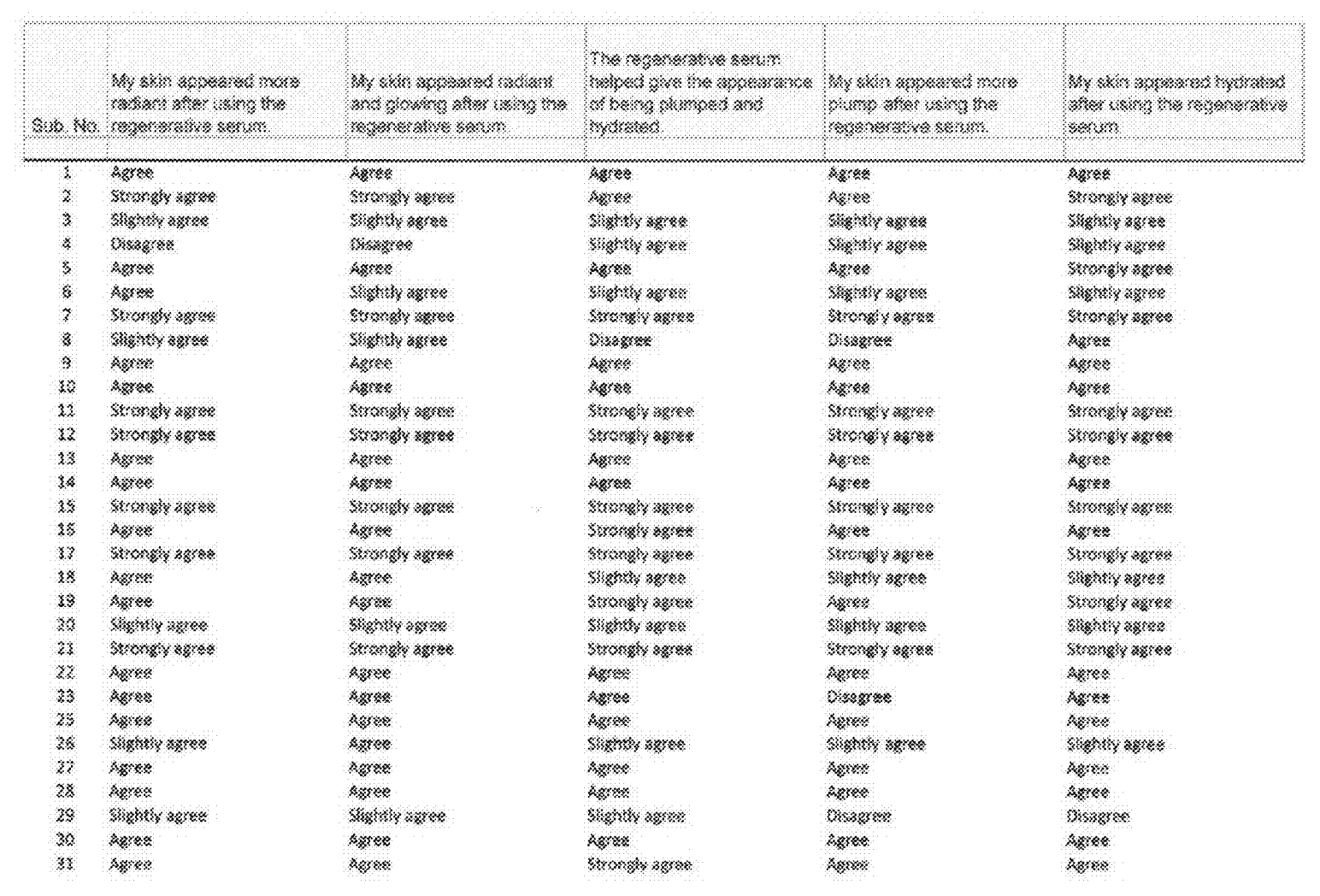

FIG. 14 is chart illustrating an example result of the implementation of one or more techniques and/or one or more systems described herein.

Figure 15:
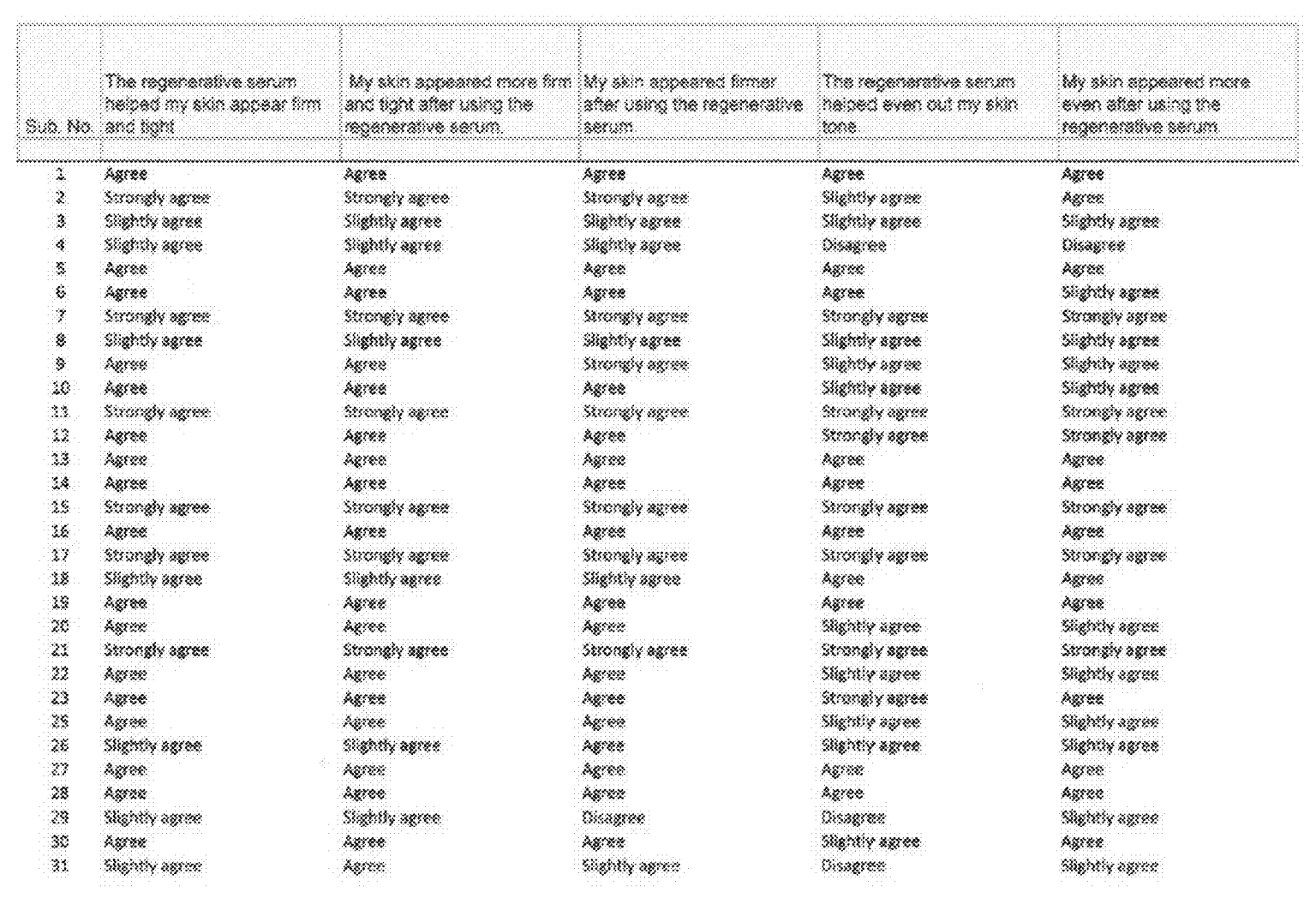

FIG. 15 is chart illustrating an example result of the implementation of one or more techniques and/or one or more systems described herein.

Figure 16:
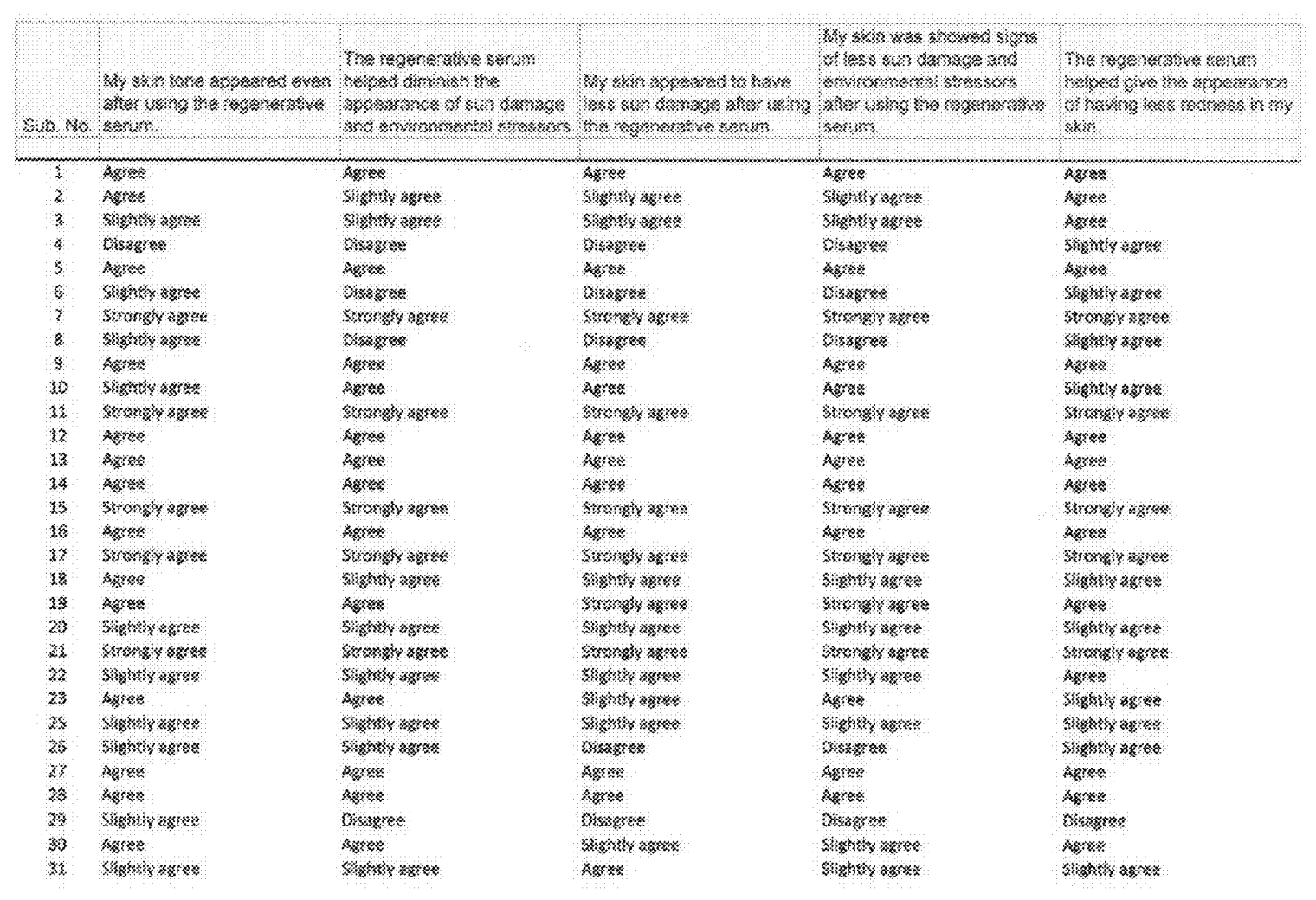

FIG. 16 is chart illustrating an example result of the implementation of one or more techniques and/or one or more systems described herein.

Figure 17:
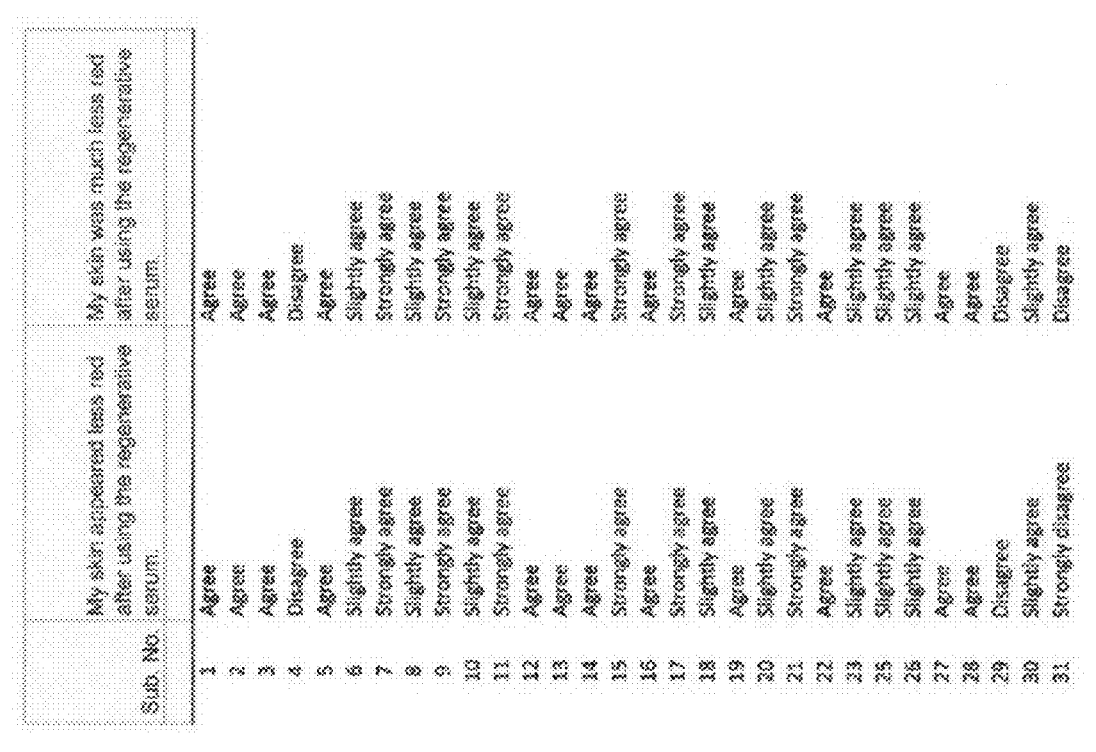

FIG. 17 is chart illustrating an example result of the implementation of one or more techniques and/or one or more systems described herein.

DETAILED DESCRIPTION

Figure 1:
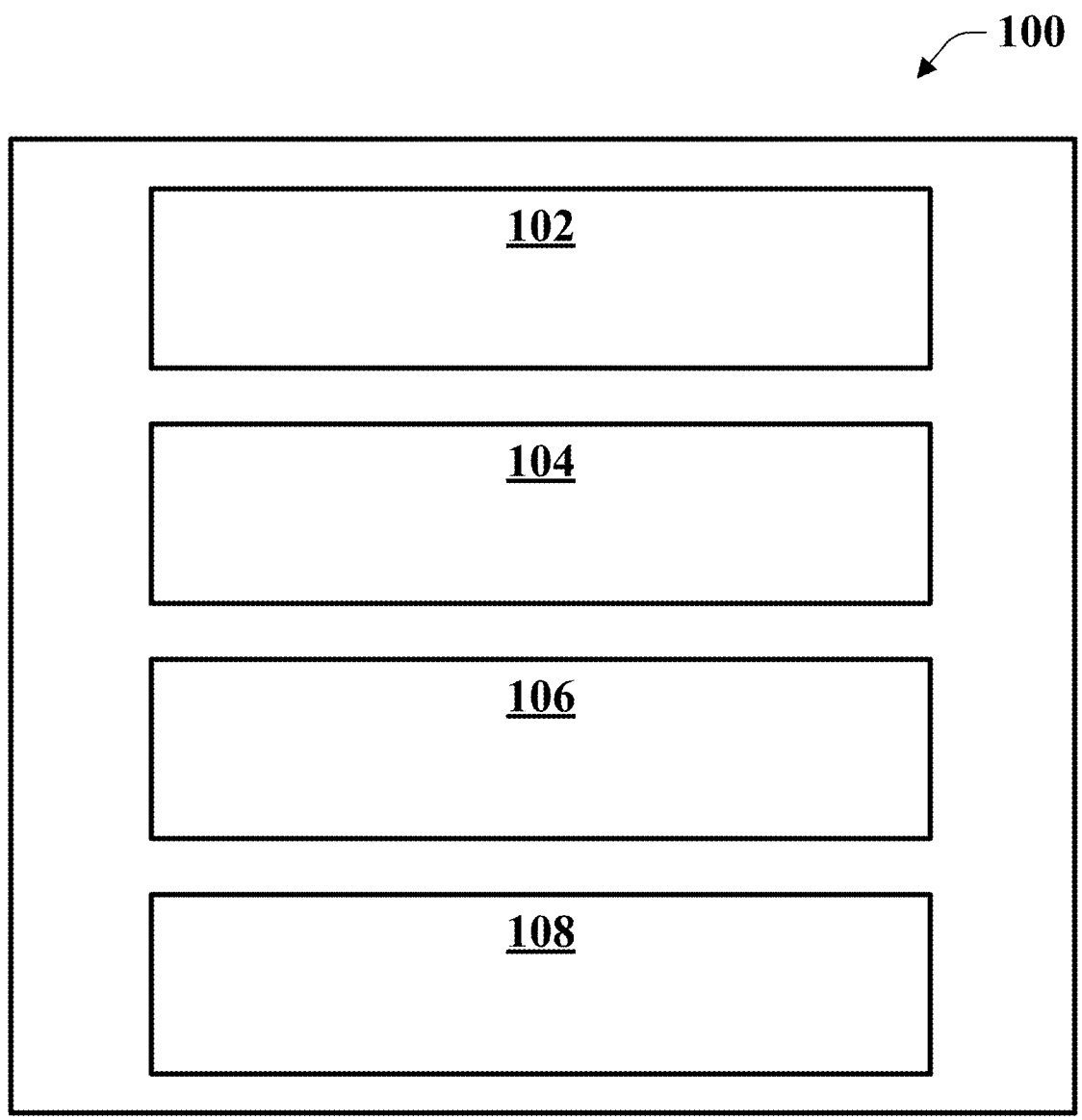
FIG. 1 is a schematic diagram of an exemplary skin care blend utilizing one or more techniques and/or one or more systems described herein.
Figure 2:
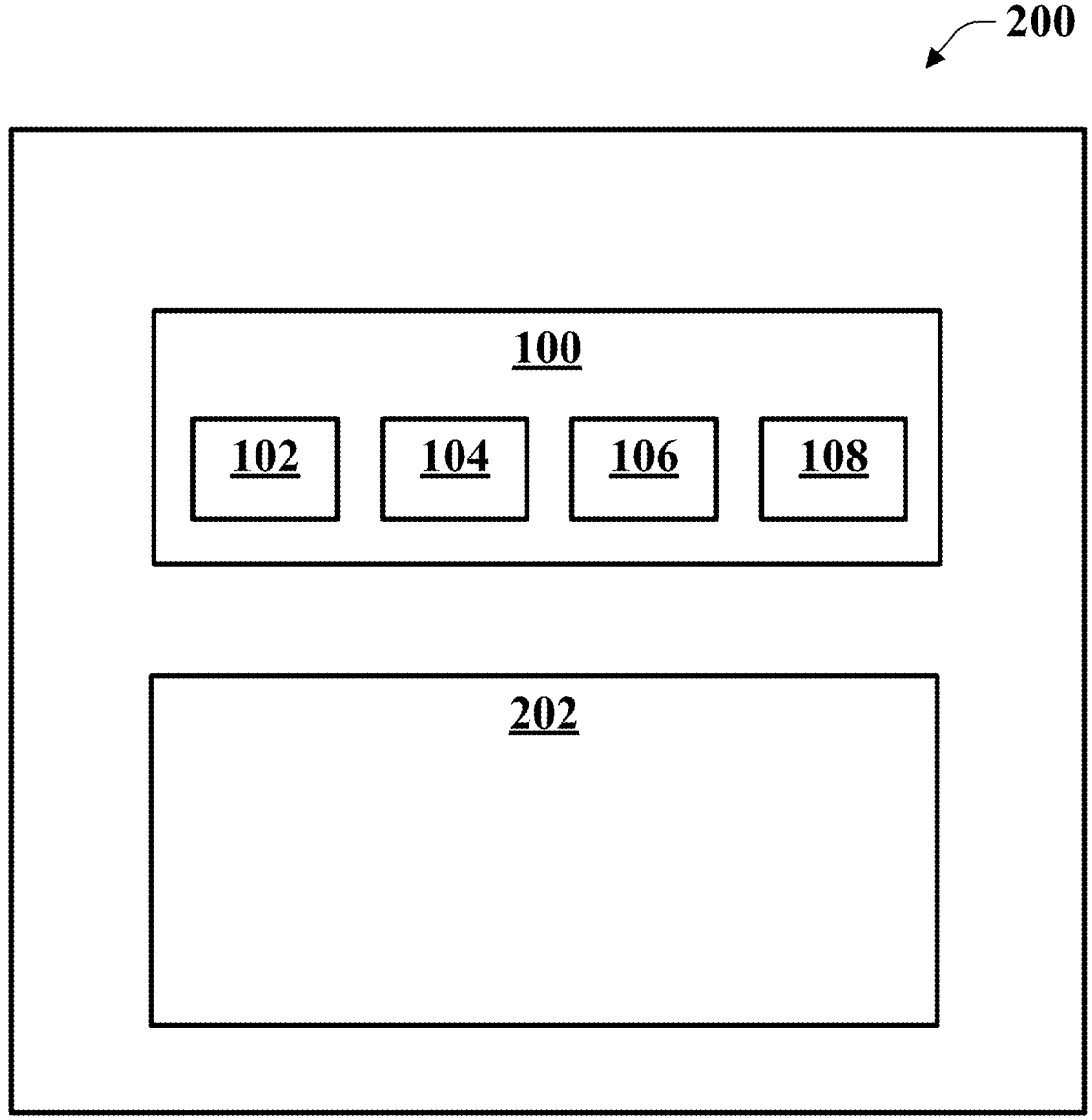
FIG. 2 is a schematic diagram of an exemplary skin care product utilizing one or more techniques and/or one or more systems described herein.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

Human skin can lose its regenerative properties and begin to show signs of aging and a decrease in healing capabilities as a person ages. This change can happen due to an abundance of molecular reactions occurring at the cellular level. The result can be a lack of skin-elasticity that causes wrinkles and/or severe scarring after trauma. Provided herein is an exemplary skin care blend and/or skin care products that can mitigate the skin aging process and/or restore damaged skin.

In an implementation, an exemplary skin care blend can comprise a synthesized protein matrix, a plurality of peptides, a plurality of amino acids, and other ingredients. In this embodiment, the synthesized protein matrix can comprise a combination of synthesized growth factors and other ingredients. The exemplary skin care blend can sometimes be referred to as a formulation of peptide-rich plasma.

In this implementation, specially formulated growth factors, essential vitamins, peptides, and amino acids are used to formulate an exemplary skin care blend. The combination of ingredients can help stressed or damaged cells grow more robust and healthier, resulting in healthier and younger looking skin. For example, the exemplary skin care blend can restore aged, stressed and wounded cells to the healthy growing state more effectively than other methods. The rejuvenation rate of the cells can be proportional to the concentration of the exemplary skin care blend, suggesting the exemplary skin care blend played a direct role in cell revival.

In another exemplary embodiment, an exemplary skin care blend can comprise a synthesized protein matrix, a native protein matrix, and additional ingredients. This exemplary skin care blend can sometimes be referred to as an active placental matrix.

In this implementation, synthesized placental proteins (a synthesized protein matrix) can be used in an exemplary skin care product. Human placental proteins have gained popularity recently for their potential regenerative effects. The effects of placental proteins may be desirable because, as skin loses its regenerative properties, it begins showing signs of aging and decreases in healing capabilities. The synthesized protein matrix can exhibit the regenerative effects of human placental proteins while also mitigating (e.g., eliminating or reducing) the risk disease transmission that can be associated with human placental proteins. For example, the exemplary skin care blend can be produced from a combination of naturally-occurring compounds, amino acids, peptides, or the like. The exemplary skin care blend can include a protein matrix or growth factors, a group of peptides, and a group of amino acids. The skin care blend can improve skin conditions and can combat signs of aging and/or improve skin regeneration after injury.

In some embodiments, the exemplary skin care blends described above can be combined with other ingredients to form an exemplary skin care product. The exemplary skin care product can be in the form of a serum, a moisturizer, eye cream, sun screen product (SPF), or similar skin care product. As an example, the exemplary skin care product can be used by applying it directly to the skin, and gently rubbing the product in for absorption to promote healthy skin and reduce the appearance of fine lines and wrinkles.

Turning to FIG. 1, a schematic diagram of an exemplary skin care blend 100 is shown. Skin care blend 100 can comprise a synthesized protein matrix 102, a plurality of peptides 104, a plurality of amino acids 106, and other ingredients 108. In this exemplary embodiment, the synthesized protein matrix 102 can comprise a combination of the following growth factors: sh-Oligopeptide-2, sh-Polypeptide-1, sh-Polypeptide-9, sh-Polypeptide-11, and sh-Oligopeptide-1. The plurality of peptides 104 can comprise the following: Palmitoyl Tripeptide-5, Palmitoyl Tetrapeptide-7, and Acetyl Hexapeptide-8. The plurality of amino acids 106 can comprise the following ingredients: Acetyl Glutamine, Lysine HCL, Alanine, Histidine HCL, Arginine, Serin, Proline, Glutamic Acid, Threonine, Valine, Leucine, Glycine, Isoleucine, Phenylalanine, and Taurine. Other ingredients 108 can comprise Vitamin B-9 and Sodium Hyaluronate. The exemplary skin care blend 100 can sometimes be referred to as a formulation of peptide-rich plasma.

In an implementation, the exemplary skin care product 200 can be a face serum. The exemplary skin care product 200 (e.g., a face serum) can comprise the exemplary skin care blend 100 and additional skin care ingredients 202. The additional skin care ingredients 202 can include a selection of vitamins, and/or other beneficial skin care ingredients. In this implementation, the additional skin care ingredients 202 comprise: Glycerin, *Hedychium Coronarium* Root Extract, Tripeptide-1, *Polygonum Aviculare* Extract, Honey, Nonapeptide-1, Acetyl Heptapeptide-4, Phytosphingosine, Sea Whip Extract, Niacinamide, Hydrolyzed Hyaluronic Acid, Aminobutyric Acid, Adenosine, Thioctic Acid, Glycolic Acid, *Bacillus*/Soybean/Folic Acid Ferment Extract, Polysorbate 20, Allantoin, Caprylyl Glycol, Lecithin, Butylene Glycol, 1,2-Hexanediol, Dextran, Phenoxyethanol, Ethylhexylglycerin, and Xanthan Gum.

In this implementation, the exemplary skin care blend 100 (e.g., a peptide-rich plasma) can contain active ingredients to promote healthy skin. It should be appreciated, however, that other active ingredients can be added to improve efficacy of the exemplary skin care product 100. For example other active ingredients can include: Nonapeptide-1, Alpha Lipoic Acid, Niacinamide, Savage Ginger Root Extract and Knotgrass Flavonoids, (Gamma aminobutyric acid) GABA, Manuka Honey, Glycolic Acid, and Hyaluronic Acid.

By way of example, Nonapeptide-1 may block melanin synthesis to target discoloration, Alpha Lipoic Acid may act as a potent antioxidant and free radical scavenger, Niacinamide may reduce redness and inflammation, and Savage Ginger Root Extract and Knotgrass Flavonoids may protect against environmental ultraviolet, infrared, or blue light damage. Further, (Gamma aminobutyric acid) GABA may include active neuropeptides for healing and repair, Manuka Honey can promote healing and skin immunity, Glycolic Acid may improve skin texture and reduce enlarged pores, and Hyaluronic Acid may improves moisture and skin plumpness. It should be appreciated that other ingredients, selected according to sound professional judgment, may be utilized along with the exemplary skin care blend 100 to form a skin care product (e.g., skin care product 200) without deviating from the scope of this application.

In an implementation, the exemplary skin care product 200 can be a moisturizer. The exemplary skin care product 200 (e.g., a moisturizer) can comprise the exemplary skin care blend 100 and additional skin care ingredients 202. Additional ingredients 202 can comprise Aqua/Water/Eau, Ethylhexyl Palmitate, *Butyrospermum Parkii* (Shea) Butter, *Cocos Nucifera* (Coconut) Oil, Cetearyl Olivate, Sorbitan Oleate, Stearyl Alcohol, Propanediol, Glyceryl Stearate, Aloe Barbadensis (Aloe) Leaf Juice, Caprylhydroxamic Acid, Caprylyl Glycol, Glycerin, *Alteromonas* Ferment Extract, Glycosphingolipids, Glycolipids, Hydrolyzed Hyaluronic Acid, Ferulic Acid, Retinyl Palmitate, Resveratrol, Ergothioneine, *Linum Usitatissimum* (Linseed) Seed Oil, *Bacillus*/Soybean/Folic Acid Ferment Extract, Tocopherol, Sodium PCA, 1,2-Hexanediol, Polysorbate 20, Ethylhexylglycerin, Allantoin, Lecithin, Butylene Glycol, *Ros-*

*marinus Officinalis* (Rosemary) Leaf Extract, *Lavandula Agustifolia* (Lavender) Oil, Xanthan Gum. In this implementation, the skin care product 200 (e.g., moisturizer) can be applied to clean skin in the morning and evening, or as needed. A user can massage into a desired location on the skin until fully absorbed.

In another implementation, the exemplary skin care product 200 can be an eye renewal cream. The exemplary skin care product 200 (e.g., eye renewal cream) can comprise the exemplary skin care blend 100 and additional skin care ingredients 202. Additional ingredients 202 can comprise Aqua/Water/Eau, Pentylene Glycol, Methylheptyl Isostearate, Beta-Glucan, Niacinamide, Trehalose, Dipeptide Diaminobutyroyl Benzylamide Diacetate, Sodium, Acrylate/Sodium Acryloyldimethyl Taurate Copolymer, Boron Nitride, Glycerin, Hesperidin, Methyl Chalcone, Dipeptide-2, N-Hydroxysuccinimide, Chrysin, Palmitoyl Tripeptide-1, Aminopropyl Ascorbyl Phosphate, Dimethylmethoxy Chromanyl Palmitate, Alpha Arbutin, Kojic Acid, *Arnica Montana* Flower Extract, *Vaccinium Myrtillus* (Bilberry) Fruit Extract, *Euterpe, Oleracea* Fruit Extract, *Lycium Barbarum* (Goji) Fruit Extract, Garcinia Mangostana Peel, Powder, Punica Granatum Fruit Powder, *Morinda Citrifolia* Leaf Powder, Biotin, Allantoin, *Bacillus*/Soybean/Folic Acid Ferment Extract, Tocopherol, Steareth-20, Chlorhexidine, Digluconate, Potassium Sorbate, Citric Acid, Sodium Citrate, Phenoxyethanol, Ethylhexylglycerin, Tocopheryl Acetate, Lecithin, Propanediol, Caprylyl Glycol, Xanthan Gum. In this implementation, the skin care product 200 (e.g., eye renewal cream) can be applied by gently patting a pea-sized amount of the skin care product 200 under and around the eyes. Application can be every morning and evening.

In an implementation, the exemplary skin care product 200 can be an SPF product. The exemplary skin care product 200 (e.g., SPF product) can comprise the exemplary skin care blend 100 and additional skin care ingredients 202. Additional ingredients 202 can comprise Water/Aqua, Zinc Oxide, *Brassica Napus* Extract, Dimethicone, Cyclopentasiloxane, Caprylic/Capric Triglyceride, Glycerin, Propanediol, Bentonite, Cetearyl Alcohol, Montmorillonite, Illite, Sodium Chloride, Xanthan Gum, Citric acid, Manuka Honey, Polyglyceryl-8 Oleate, Polyhydroxystearic Acid, Dimethicone/Vinyl Dimethicone Crosspolymer, Lecithin, *Bacillus*/Folic Acid/Soybean Ferment Extract, Caprylyl Glycol, Butylene Glycol, 1,2-Hexanediol, Caprylyl Glycol, Allantoin, Hyaluronic Acid, Dimethylmethoxy Chromanyl Palmitate, *Caesalpinia Spinosa* Fruit Pod Extract, *Helianthus Annuus* (Sunflower) Sprout Extract, Maltodextrin, Lactic Acid, Phenoxyethanol, Ethylhexylglycerin. In this implementation, the skin care product 200 (e.g., SPF product) can be applied to the face, neck and chest in the morning. For example, two pumps of the product can be applied to the hand and gently massaged into the skin.

Figure 3:
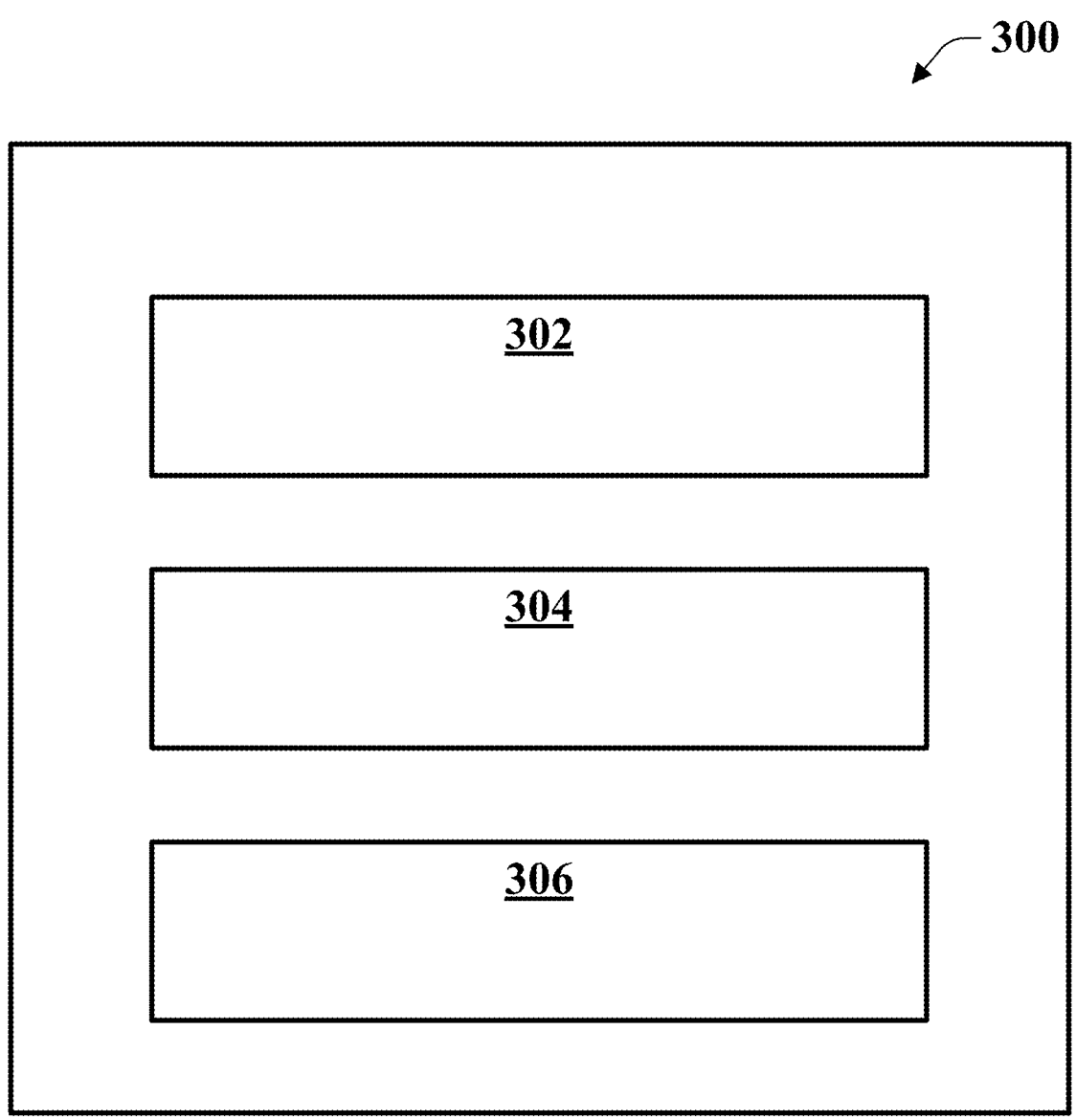
FIG. 3 is a schematic diagram of an exemplary skin care product utilizing one or more techniques and/or one or more systems described herein.

Turning to FIG. 3, a schematic diagram of an exemplary skin care product 300 is shown. The skin care product 300 can be a skin moisturizer comprising a synthesized protein matrix 302, a native protein matrix 304, and additional skin care ingredients 306. In this exemplary embodiment, the synthesized protein matrix 302 can comprise the following ingredients and growth factors: epidermal growth factor (EGF); insulin-like growth factor-1 (IGF-1), acidic fibroblast growth factor (FGF), basic FGF, vascular endothelial growth factor (VEGF), vitamin B9, and acetyl glutamine.

In this embodiment, the native protein matrix 304 can be synthesized from human tissue conditioned media. The native protein matrix 304 can comprise human fibronectin, human collagen, human thrombospondin, human actin cytoplasmic, and human elastin. The native protein matrix 304 can be combined with other ingredients such as the synthesized protein matrix 302 to form the exemplary skin care product 300. It should be appreciated that the native protein matrix 304 can be utilized in combination with a synthesized protein matrix 302, skin care blend 100, skin care product 200, any other skin care product, or may not be used at all.

For example, in an implementation described herein, the exemplary skin care product 300 can comprise the synthesized protein matrix 302 that has been generated from microbial bio-fermentation. The synthesized protein matrix 302 can comprise epidermal growth factor (EGF), insulin-like growth factor-1 (IGF-1), acidic fibroblast growth factor (FGF), basic FGF, vascular endothelial growth factor (VEGF), vitamin B9, and acetyl glutamine. Further, in this implementation, the exemplary skin care product 300 can comprise a native protein matrix 304 comprising human fibronectin, human collagen, human thrombospondin, human actin cytoplasmic, and human elastin. Additionally, the exemplary skin care product 300 can comprise any or all of the following additional ingredients 306: shea butter, coconut oil, aloe, linseed oil, ergothioneine, vitamin A, vitamin C, vitamin E, resveratrol, Coenzyme Q10, and ferulic acid.

In other embodiments, the skin care products (e.g., 200, 300) can include additional nourishing ingredients or vitamins. For example, additional ingredients 202, 306 can include any or all of the following: shea butter, coconut oil, aloe, linseed oil, ergothioneine, vitamin A, vitamin C, vitamin E, resveratrol, Coenzyme Q10, and ferulic acid. Further, the additional skin care ingredients 202, 306 can include: Glycerin, *Hedychium Coronarium* Root Extract, Tripeptide-1, *Polygonum Aviculare* Extract, Honey, Nonapeptide-1, Acetyl Heptapeptide-4, Phytosphingosine, Sea Whip Extract, Niacinamide, Hydrolyzed Hyaluronic Acid, Aminobutyric Acid, Adenosine, Thioctic Acid, Glycolic Acid, *Bacillus*/Soybean/Folic Acid Ferment Extract, Polysorbate 20, Allantoin, Caprylyl Glycol, Lecithin, Butylene Glycol, 1,2-Hexanediol, Dextran, Phenoxyethanol, Ethylhexylglycerin, and/or Xanthan Gum. It should be appreciated that other nourishing ingredients or vitamins can be added to the skin care products 200, 300 according to sound professional judgment without deviating from the scope of the present application.

In one example, human placental proteins can have desirable regenerative properties when used on human skin. The use of human placental tissues, however, is restricted in select countries due to risks of disease transmission. Other counties allow use of human placental proteins in skin care products, but the process can be complicated. These complications can make the use of human placental proteins undesirable. For instance, human placental proteins contain estrogen, which can be carcinogenic. In light of these issues, a process of capturing the regenerative properties of human placental proteins, without the risks associated with their use, can be desirable in the skin care and/or medical field.

In an exemplary embodiment, a portion of placental tissue that contains skin actives (e.g., a protein-rich mixture of peptides, growth factors, and the like) can be isolated from a portion of inactive placental tissue (e.g., cells, collagen, etc.). In this manner, the portion of active, beneficial cells can be isolated from the inactive tissue/cells. By way of example, the active portion of isolated tissue contains desirable growth factors and proteins, but does not contain cells, collagen, estrogen, or other undesirable portions. In this embodiment, a synthesized protein matrix can be derived from the isolated portion of active placental proteins.

In one implementation, the synthesized protein matrix 302 can be formed through a manufacturing process that results in an array of growth factors. For example, the growth factors and/or the synthesized protein matrix can be manufactured using human tissue cultured media and via microbial bio-fermentation. In this implementation, genes can be synthesized by a polymerase chain reaction, where the genes can be injected with recombinant *E. coli* that causes proliferation and fermentation. This substance can then be purified to obtain the desired growth factors. Using this process, a synthesized matrix of proteins, peptides, immunostimulants, and growth factors can be formulated that mimics the same protein composition as human placental tissue. By mimicking the active protein composition of live human placental tissue, the synthesized protein matrix 302 can achieve similar, if not enhanced, regenerative and anti-aging benefits.

In an implementation described herein, growth factors can achieve desired biological effects on human skin. For example, some growth factors have been identified as useful in wound healing and/or epidermal remodeling include. For instance, human skin may see benefits from transforming growth factor-β (TGF-β), epidermal growth factor (EGF), insulin-like growth factors (IGFs), platelet-derived growth factor (PDGF), and fibroblast growth factors (FGFs). Because growth factors can obtain desired regenerative effects on human skin, at least one growth factor can be utilized in skin care products. It should be appreciated that at least one or a plurality of growth factors can be used. For instance, the following exemplary growth factors can be used: EGF, PDGF, FGF, TGF-β, TGF-α, NGF, Epo, IGF-I, IGF-II, IL1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-α, TNF-β, GM-CSF, and M-CSF, or a combination thereof. In an exemplary embodiment, a growth factor combination can be formed from epidermal growth factor (EGF); insulin-like growth factor-1 (IGF-1), acidic fibroblast growth factor (FGF), basic FGF, vascular endothelial growth factor (VEGF).

In one implementation, an essential vitamin used in skin care blend is B9-Vitapol. In this implementation, the formation of B9-Vitapol is made through structural changes of folic acid to improve pH sensitivity and low solubility of folic acid.

In another implementation, an essential amino acid used in the skin care blend is Hydracell Q. In this implementation, Acetylated Glutamine is reformulated to improve stability, thus resulting in Hydracell Q.

In one implementation, the exemplary skin care blend 100, can be made into a serum (e.g., skin care product 200) using the techniques described herein. In this implementation, other nourishing and healing products can be combined with the skin care blend 100 to further promote restoration of skin and reversal of visible signs of aging. As an example, the exemplary skin care blend 100 or skin care product 200 can be combined with Manuka honey to provide further nourishing of the skin.

In one implementation, the exemplary skin care blend 100 can be utilized to formulate a moisturizer, where products that encourage moisture absorption are combined with the skin care blend 100 or the synthesized protein matrix 302 to achieve hydrated skin and promote skin elasticity. As an example, the exemplary skin care product blend 100 or synthesized protein matrix 303 can be combined with hyaluronic acid and shea butter to provide an increase in hydration and stimulation of cells.

In one implementation, the exemplary skin care product 300 is a moisturizer. In this implementation, the moisturizer can be applied topically to the skin in the mornings and/or evenings. Similarly, the exemplary skin care product 200 can be a face serum. In this implementation, the serum can be applied topically to the skin in mornings and/or evenings. Further in regard to a serum, a user can apply one pipette length of the serum onto their fingertips and can gently sweep over the face and neck in an upward motion. Or, in some implementations, a user can apply four to five drops of serum to a fingertip and gently massage into the face. For best effects, if using the serum and a moisturizer concurrently, the user can allow the serum to absorb into the skin before applying the moisturizer.

By way of example, the exemplary skin care blends (e.g., skin care blend 100) and/or products (e.g., skin care product 200, 300) described herein can have both medical and cosmetic uses beyond what is described above. For example, in regard to medical uses, the products described herein may be applicable for: would healing, non-healing ulcers, post-skin cancer wounds, post-radiation sores, and the like. In regard to cosmetic uses, the products described herein may be beneficial if applied after micro needle procedures or after laser resurfacing. It should be appreciated that the examples provided herein are meant to be non-limiting and other similar uses may exist.

A clinical efficacy and consumer perception evaluation has been performed to evaluate the effects of the exemplary skin care product 200 on a user's skin. Results from the clinical study are illustrated in FIGS. 5-24. In this clinical study the exemplary skin care product 200 is a face serum. The results show that the face serum can achieve nourishing and regenerative effects on a user's skin. The face serum that was analyzed comprises: Aqua/Water/Eau, Pentylene Glycol, exemplary skin care blend 100 (e.g. peptide-rich plasma), Glycerin, *Hedychium Coronarium* Root Extract, Tripeptide-1, *Polygonum Aviculare* Extract, Honey, Nonapeptide-1, Acetyl Heptapeptide-4, Phytosphingosine, Sea Whip Extract, Niacinamide, Hydrolyzed Hyaluronic Acid, Aminobutyric Acid, Adenosine, Thioctic Acid, Glycolic Acid, *Bacillus*/Soybean/Folic Acid Ferment Extract, Polysorbate 20, Allantoin, Caprylyl Glycol, Lecithin, Butylene Glycol, 1,2-Hexanediol, Dextran, Phenoxyethanol, Ethylhexylglycerin, Xanthan Gum. The synthesized protein matrix comprises: sh-Oligopeptide-2, sh-Polypeptide-1, sh-Polypeptide-9, sh-Polypeptide-11, Acetyl Hexapeptide-8, sh-Oligopeptide-1, Palmitoyl Tripeptide-5, Palmitoyl Tetrapeptide-7, Acetyl Glutamine, Sodium Hyaluronate, Lysine HCL, Alanine, Histidine HCL, Arginine, Serine, Proline, Glutamic Acid, Threonine, Valine, Leucine, Glycine, Isoleucine, Phenylalanine, and Taurine.

In the clinical study described above, thirty female participants aged 35-65 underwent a clinical trial lasting four weeks. The study was conducted in accordance with the intent and purpose of Good Clinical Practice regulations described in Title 21 of the US Code of Federal Regulations. The participants were required to answer a questionnaire regarding the skin care product at the end of the four week period.

For the study, subjects were enrolled in accordance with the following inclusion or exclusion criteria. Inclusion criteria included: females between the ages of 35-65 years in general good health (no physical required); individuals who could read, understand and sign the Informed Consent form; women who were able to return to the clinic at the required intervals; individuals with anticipated ability to follow the study directions, to participate in the study, to return for all visits and to apply the product as per instructions; women who were regular users of face products. Exclusion criteria included: women who were pregnant, planning a pregnancy, lactating and/or nursing a child; individuals with any visible skin disease; individuals with sunburn, suntan on the face or planning a vacation with sun-exposure or planning the use of a tanning booth during the course of the study; individuals engaged in a concurrent research project of a facial product; individuals taking medications that might have interfered with the test results, including the use of steroidal/non-steroidal anti-inflammatory drugs or antihistamines; individuals who had undergone a laser resurfacing or dermabrasion procedure on the face in the past 2 years or a chemical face peel (deep peel in the past 1 year; superficial peel in the past 2 months); individuals with acne, active atopic dermatitis/eczema or psoriasis; individuals who had had a surgical cosmetic procedure on the face within the past 10 years; treatment or history of any type of cancer; individuals who were under treatment for asthma or diabetes; individuals with a known sensitivity to cosmetics or personal care products.

The study was designed as a four week study in which the participants would apply the test serum according to the care instructions provided by the test sponsor. The participants reported to a testing facility at the start of the study. While at the testing facility, a trained technician performed a skin test on the subjects' skin for firmness and elasticity. The participants then proceeded to apply the test serum every day (morning and evenings) for four weeks. At the end of the four week period, the participants reported back to the test facility to undergo a final measurement and evaluation. Participants also completed a survey/questionnaire to evaluate the test serum. The questionnaire presented specific questions about the use of the product and provided the participants the ability to answer according the following answer choices: strongly agree, agree, slightly agree, disagree, or strongly disagree.

The participants were given a diary and specific application instructions. Each diary entry was to include the date and time the product was used and any comments or observations. Instructions were provided to apply four to five drops on the fingertips and gently sweep over the face. Instructions were provided stating that the participants were not to use the test skin care product with any other serum or with any new skin care products (e.g., products that were not used by the participant prior to the study).

Results from the clinical study described above have shown that the exemplary embodiment of a face serum has multiple benefits to a user/patient's skin, as illustrated in FIGS. 5-24. For instance, 100% of clinical participants agree that the serum helps to smooth fine lines and wrinkles, 95% agree that the serum helps to reduce the size of pores, 99% state that their skin appeared less dull, 96% agree that the serum helps to make skin look brighter, 96% agree that the serum gave their skin an instant glow, and 95% state that their skin appeared more radiant. Other results show that 89% agree that the serum helped to even out skin tone, 90% state that their skin appeared more plump, 96% state that their skin appeared more hydrated, and 96% state that their skin appeared more plump and hydrated. Still, other results show that 100% agree that their skin appeared more firm and tight, 82% state that their skin appeared to have less sun damage, 84% stated that their skin showed sign of less sun damage and environmental stressors, ad 87% agree that the serum helped to diminish the appearance of sun damage and environmental stressors.

By way of example, a second clinical efficacy and consumer perception evaluation has been performed to evaluate the effects of the exemplary skin care product 200 on a user's skin. Results from the second clinical study are illustrated in FIGS. 25-30. In this clinical study the exemplary skin care product 200 is an eye renewal cream. The results show that the eye renewal cream can achieve nourishing and regenerative effects on a user's skin. The eye cream that was analyzed comprises: exemplary skin care blend 100 (peptide rich plasma), Aqua/Water/Eau, Pentylene Glycol, Methylheptyl Isostearate, Beta-Glucan, Niacinamide, Trehalose, Dipeptide Diaminobutyroyl Benzylamide Diacetate, Sodium, Acrylate/Sodium Acryloyldimethyl Taurate Copolymer, Boron Nitride, Glycerin, Hesperidin, Methyl Chalcone, Dipeptide-2, N-Hydroxysuccinimide, Chrysin, Palmitoyl Tripeptide-1, Aminopropyl Ascorbyl Phosphate, Dimethylmethoxy Chromanyl Palmitate, Alpha Arbutin, Kojic Acid, *Arnica Montana* Flower Extract, *Vaccinium Myrtillus* (Bilberry) Fruit Extract, *Euterpe, Oleracea* Fruit Extract, *Lycium* Barbarum (Goji) Fruit Extract, Garcinia Mangostana Peel, Powder, Punica Granatum Fruit Powder, *Morinda Citrifolia* Leaf Powder, Biotin, Allantoin, *Bacillus*/Soybean/Folic Acid Ferment Extract, Tocopherol, Steareth-20, Chlorhexidine, Digluconate, Potassium Sorbate, Citric Acid, Sodium Citrate, Phenoxyethanol, Ethylhexylglycerin, Tocopheryl Acetate, Lecithin, Propanediol, Caprylyl Glycol, Xanthan Gum.

In this study, for example, results show that 97% of participants agree that the eye renewal cream helps to diminish dark circles under the eyes, 81% of participants agree that the eye renewal cream helped reduce puffiness around the eyes, and 91% of participants agree that the eye renewal cream helps to smooth fine lines and wrinkles. Further, the study shows that 81% of participants agree that the skin around their eyes appeared visibly tighter, 84% agreed that the eye renewal cream helped give the appearance of being plumped and hydrate, and 78% agreed that the eye renewal cream left the skin around their eyes glowing. As detail above, the clinical results show that the exemplary skin care product 200 (e.g., an eye cream) may have numerous positive and desired effects on the skin around a user's eyes.

Figure 4:
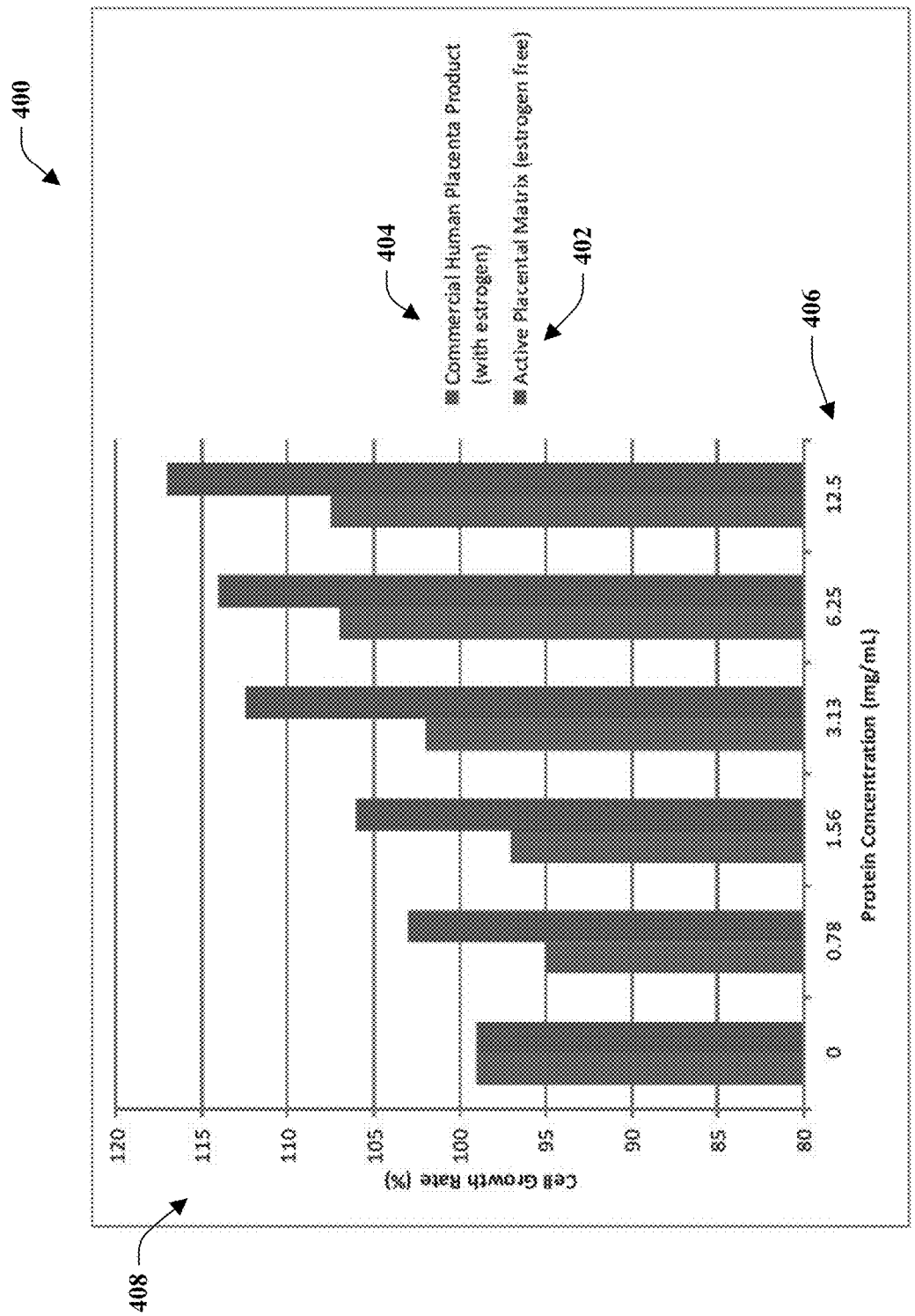
FIG. 4 is a graph illustrating an example result of the implementation of one or more techniques and/or one or more systems described herein.
Figure 10:
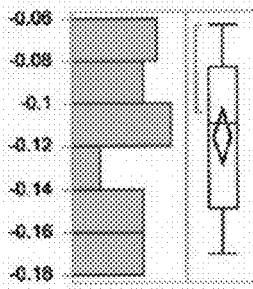
FIG. 10 is chart illustrating an example result of the implementation of one or more techniques and/or one or more systems described herein.
Figure 18:
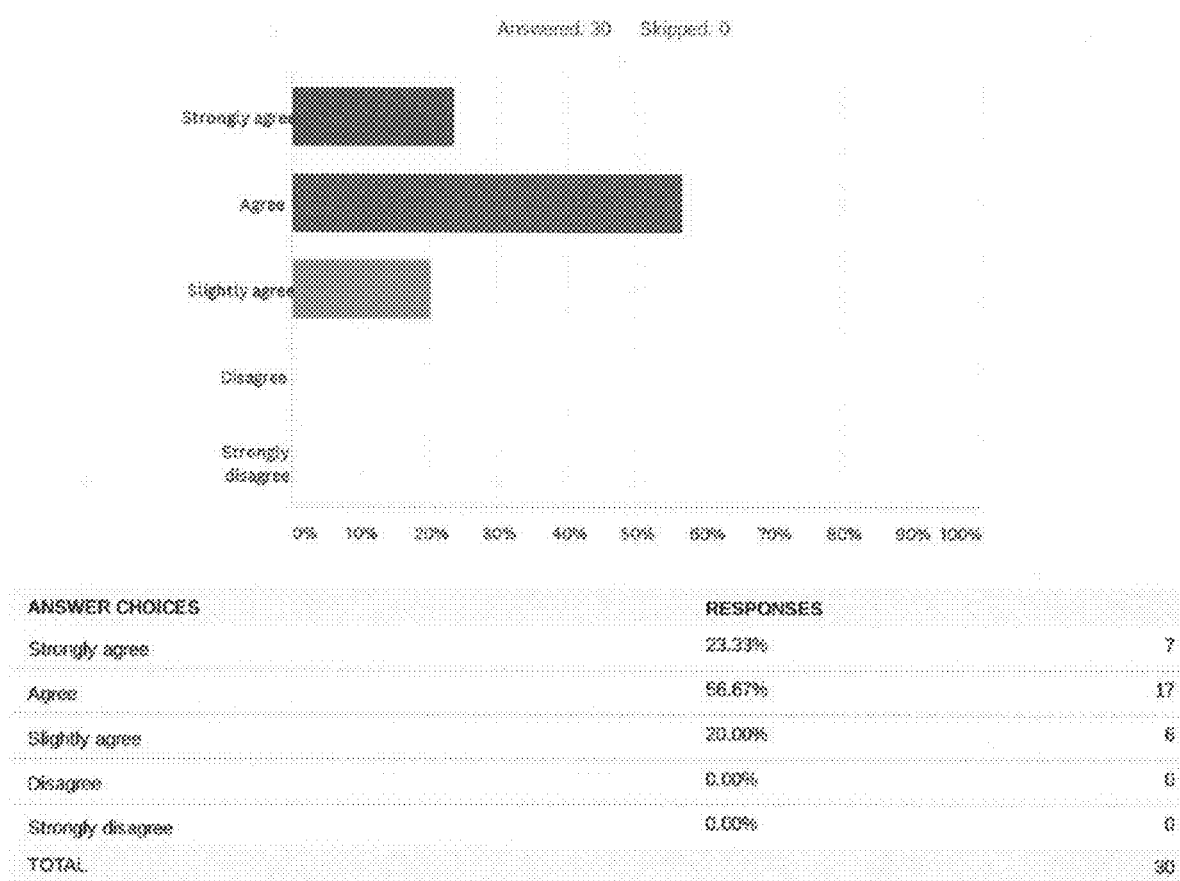
FIG. 18 is graph illustrating an example result of the implementation of one or more techniques and/or one or more systems described herein.
Figure 19:
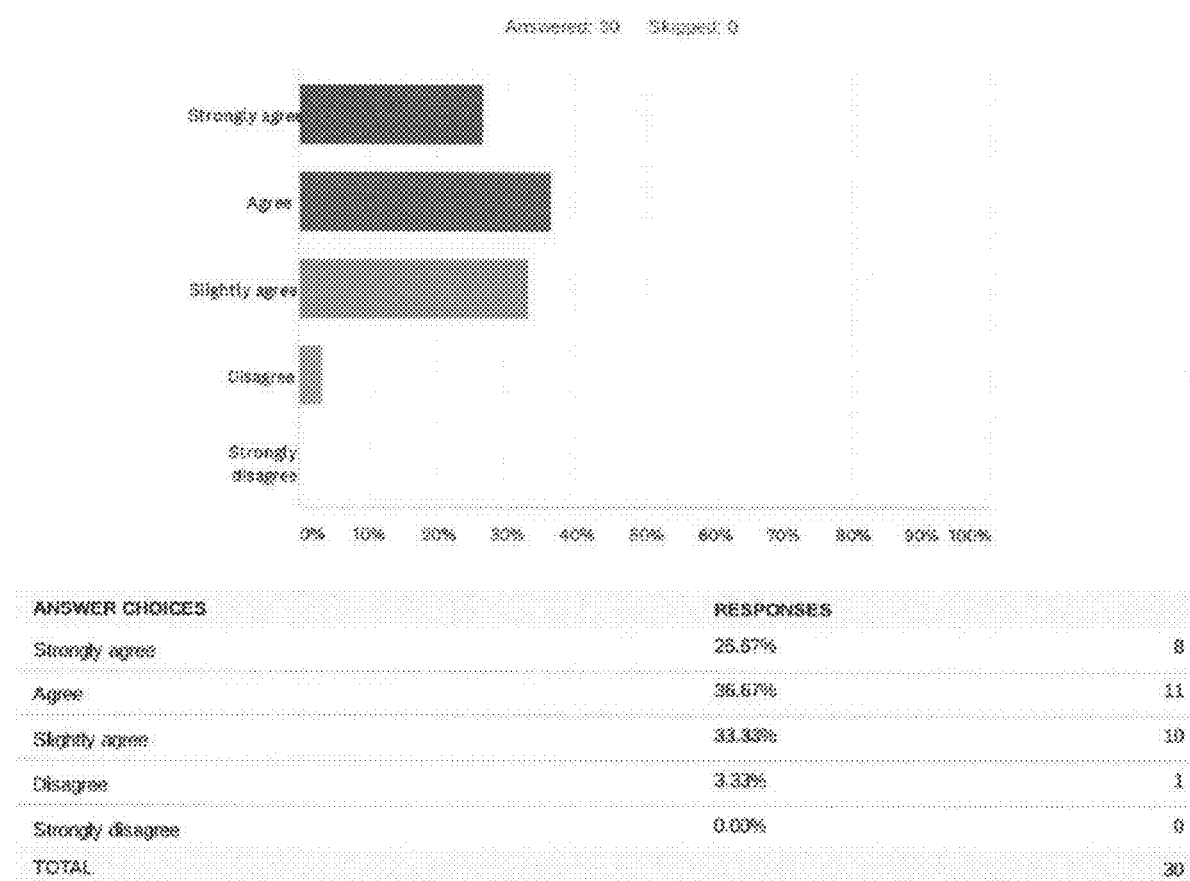
FIG. 19 is graph illustrating an example result of the implementation of one or more techniques and/or one or more systems described herein.
Figure 20:
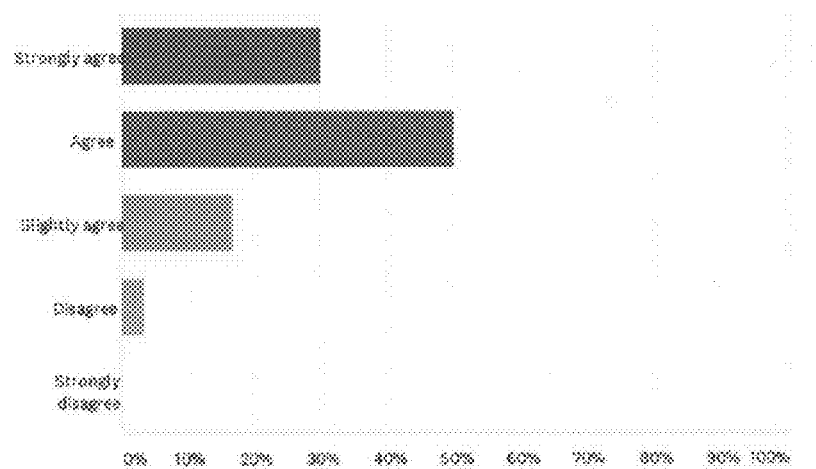
FIG. 20 is graph illustrating an example result of the implementation of one or more techniques and/or one or more systems described herein.
Figure 21:
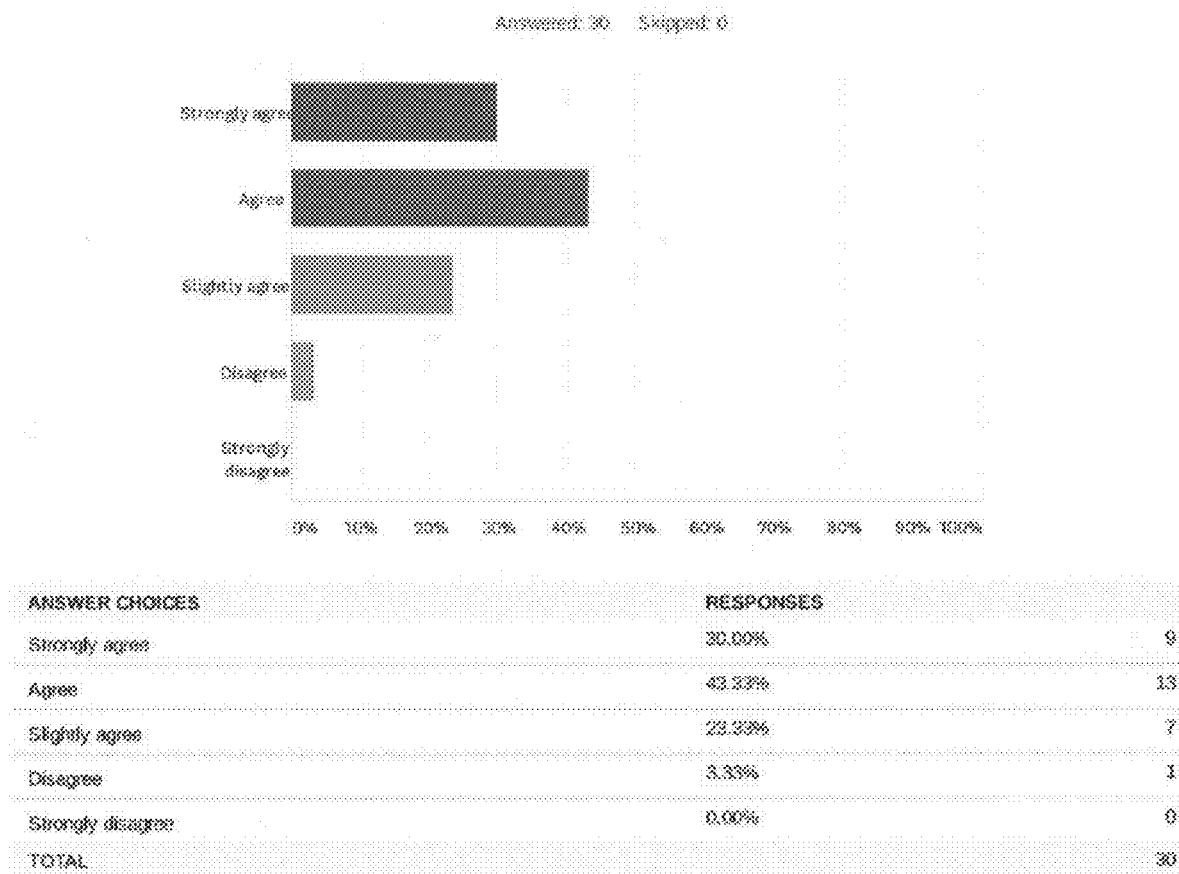
FIG. 21 is graph illustrating an example result of the implementation of one or more techniques and/or one or more systems described herein.
Figure 22:
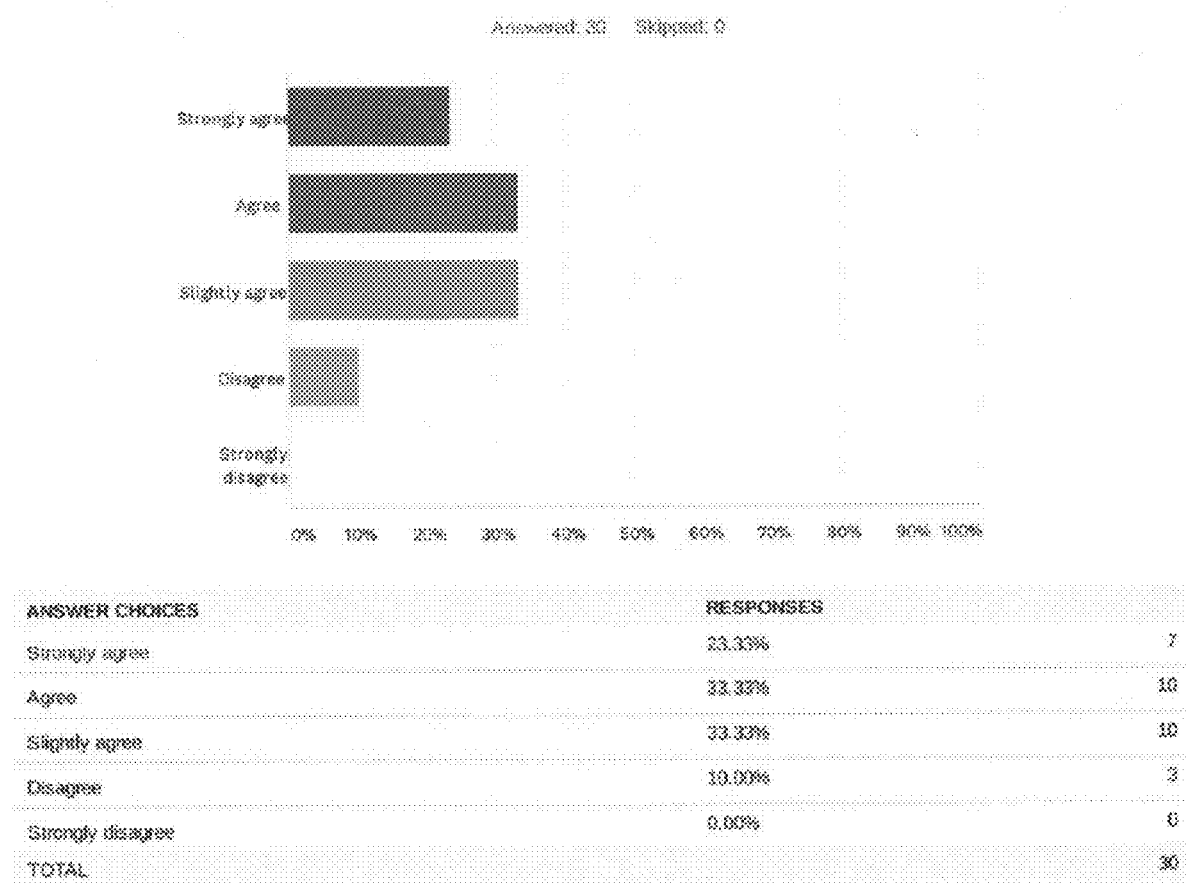
FIG. 22 is graph illustrating an example result of the implementation of one or more techniques and/or one or more systems described herein.
Figure 23:
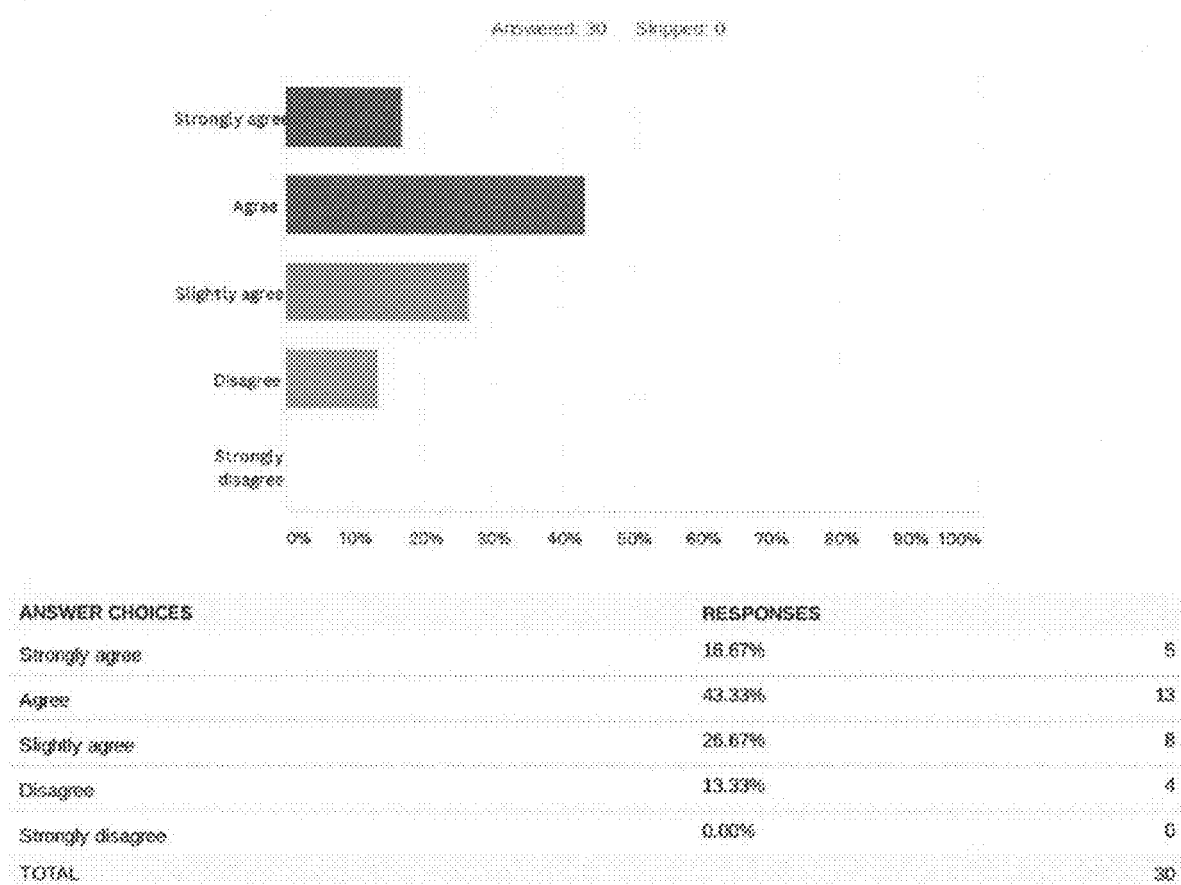
FIG. 23 is graph illustrating an example result of the implementation of one or more techniques and/or one or more systems described herein.
Figure 24:
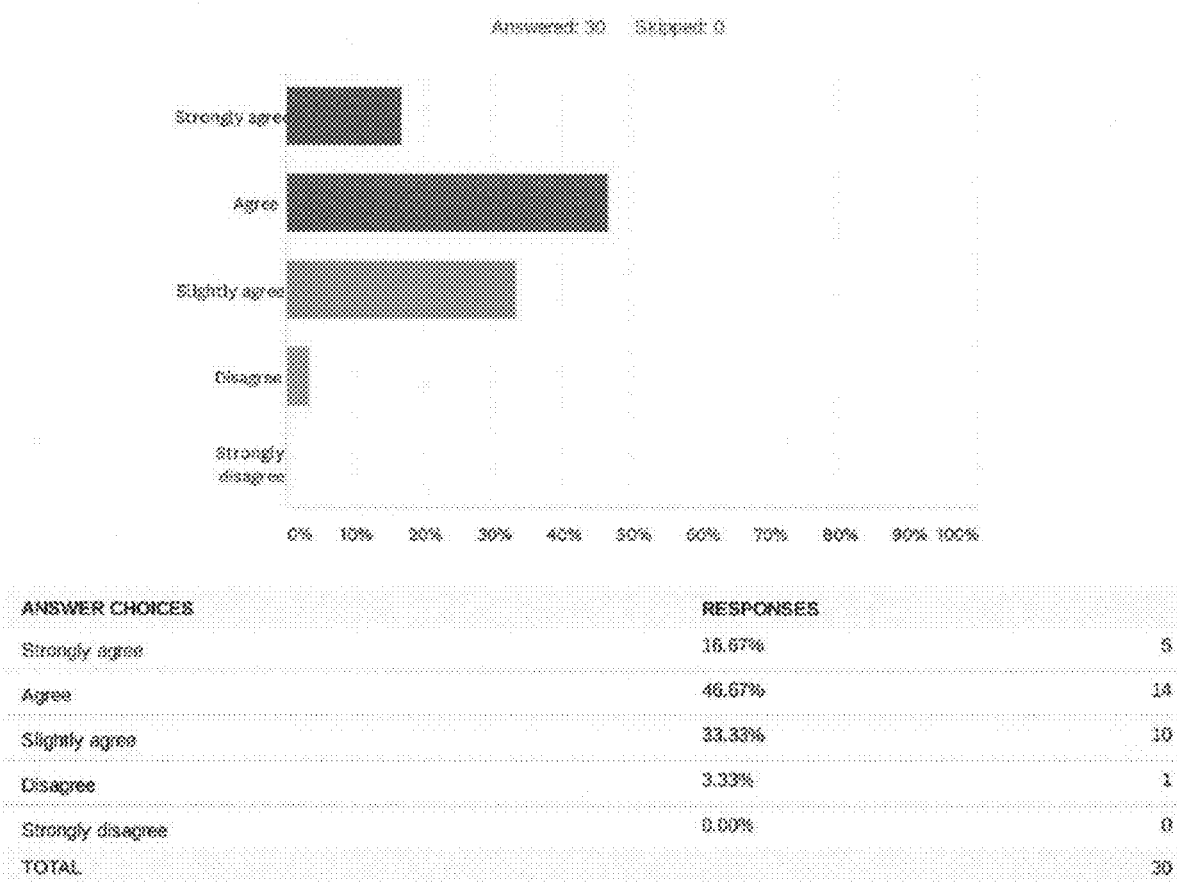
FIG. 24 is graph illustrating an example result of the implementation of one or more techniques and/or one or more systems described herein.
Figure 25:
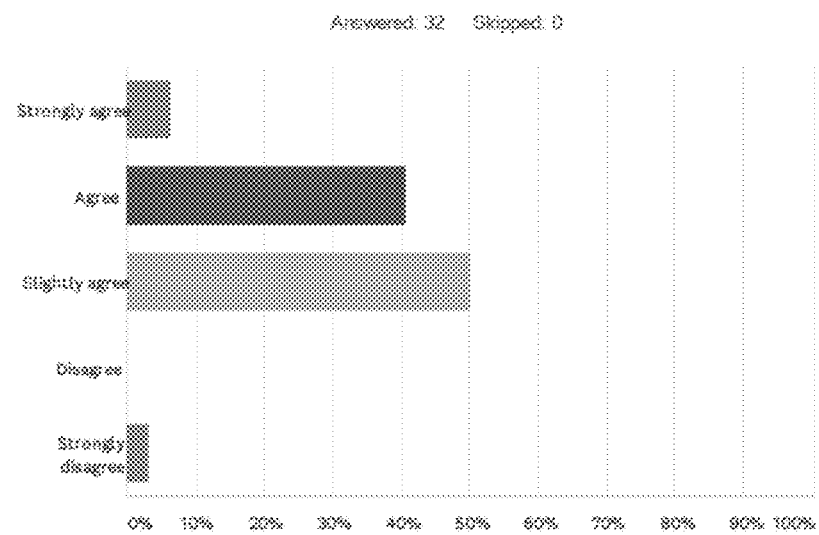
FIG. 25 is graph illustrating an example result of the implementation of one or more techniques and/or one or more systems described herein.
Figure 26:
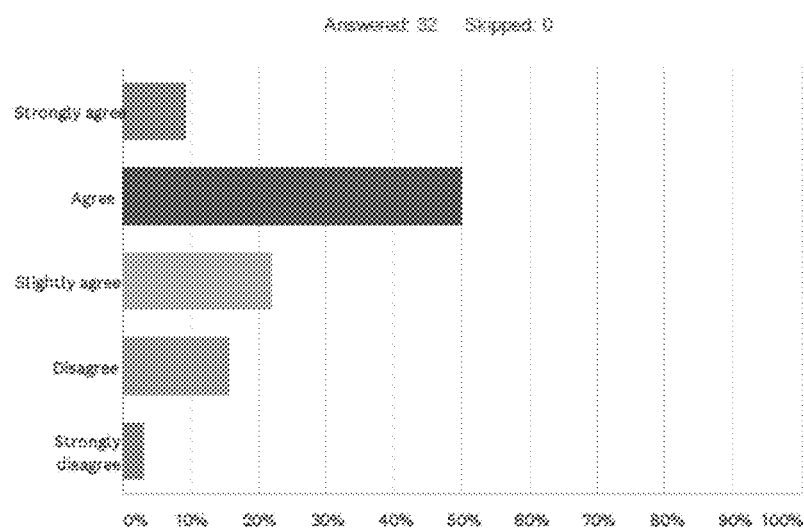
FIG. 26 is graph illustrating an example result of the implementation of one or more techniques and/or one or more systems described herein.
Figure 27:
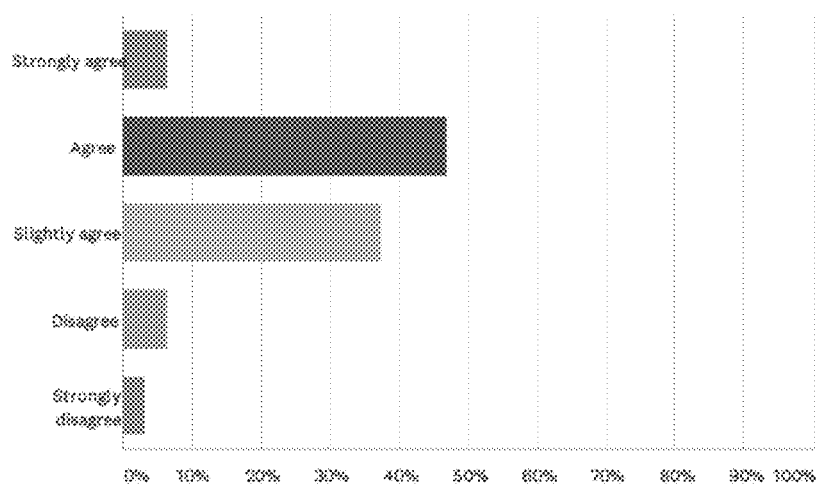
FIG. 27 is graph illustrating an example result of the implementation of one or more techniques and/or one or more systems described herein.
Figure 28:
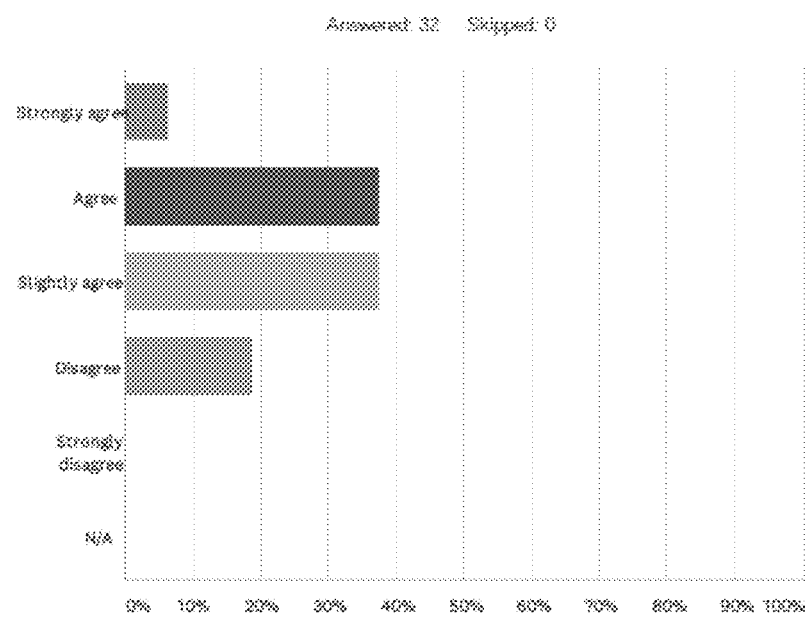
FIG. 28 is graph illustrating an example result of the implementation of one or more techniques and/or one or more systems described herein.
Figure 29:
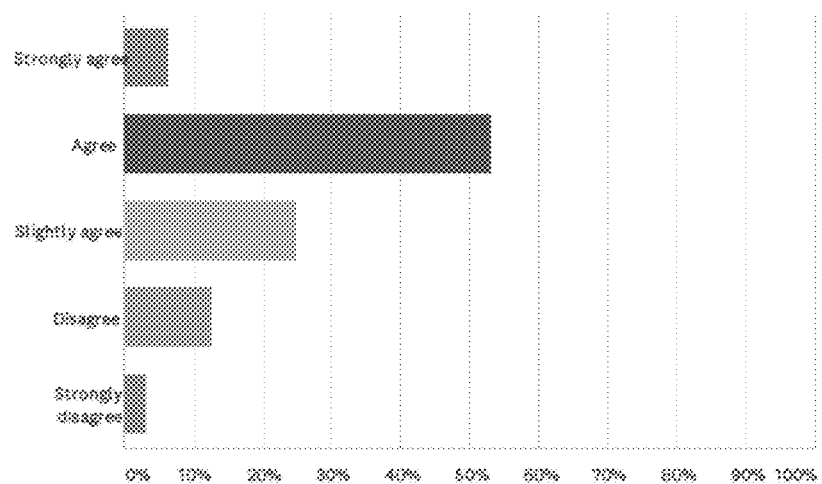
FIG. 29 is graph illustrating an example result of the implementation of one or more techniques and/or one or more systems described herein.
Figure 30:
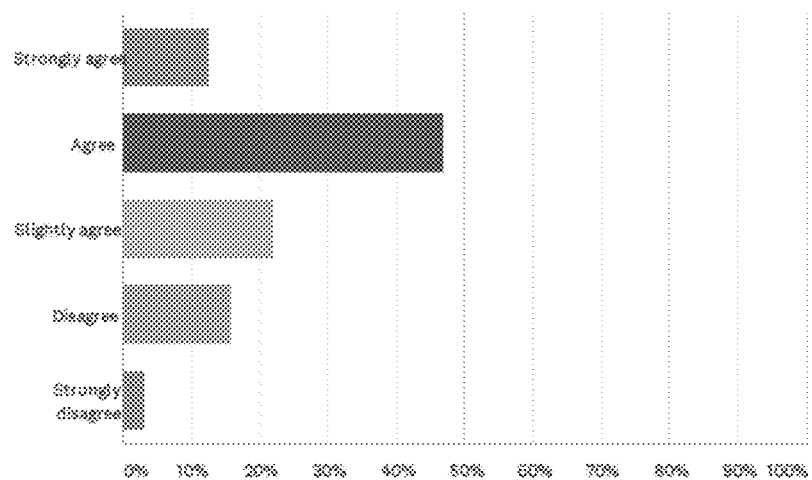
FIG. 30 is graph illustrating an example result of the implementation of one or more techniques and/or one or more systems described herein.

In one implementation, the exemplary skin care product 300 can be shown to be more effective than current, commercial, or human placental product. As illustrated in FIG. 4, results of side-by-side testing yields improved results in cell growth. Graph 400 illustrates that as the concentration 406 of the placental protein(s) are increased in the exemplary placental product (e.g., skin care product 300), an increase in cell growth rate 408 is shown. The growth rate of the synthesized protein matrix 402 is shown to be greater than the current, commercial placental product 404. In this implementation, the cell strain is Human Derma Fibroblast neonatal, and the detection method is MTT assay. In this implementation, the exemplary skin care product 402 stimulates cell growth more than commercial placental products 404.

Moreover, the word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, At least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

Furthermore, the claimed subject matter may be implemented as a method, apparatus or article of manufacture using standard engineering techniques to produce to implement the disclosed subject matter. Of course, those skilled in the art will recognize many modifications may be made to this configuration without departing from the scope or spirit of the claimed subject matter. The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A skin care product, comprising:
a synthesized protein matrix and a native protein matrix;
wherein the synthesized protein matrix comprises:
epidermal growth factor;
insulin-like growth factor-1;
acidic fibroblast growth factor;
basic fibroblast growth factor;
vascular endothelial growth factor;
vitamin B9; and
acetyl glutamine, and
wherein the skin care product further comprises glycerin, *Hedychium coronarium* root extract, tripeptide-1, *Polygonum aviculare* extract, honey, nonapeptide-1, acetyl heptapeptide-4, phytosphingosine, sea whip extract, niacinamide, hydrolyzed hyaluronic acid, aminobutyric acid, adenosine, thioctic acid, glycolic acid, folic acid ferment extract, polysorbate 20, allantoin, caprylyl glycol, lecithin, butylene glycol, 1,2-hexanediol, dextran, phenoxyethanol, ethylhexylglycerin, and xanthan gum.

2. The skin care product of claim 1, wherein the synthesized protein matrix is generated from microbial bio-fermentation.

3. The skin care product of claim 1, wherein the native protein matrix is synthesized from human tissue conditioned media.

4. The skin care product of claim 3, wherein the native protein matrix comprises human fibronectin, human collagen, human thrombospondin, human actin cytoplasmic, and human elastin.

5. The skin care product of claim 1, further comprising Manuka honey.

6. The skin care product of claim 4, further comprising:
shea butter, coconut oil, aloe, linseed oil, ergothioneine, vitamin A, vitamin C, vitamin E, resveratrol, coenzyme Q10, and ferulic acid.

7. The skin care product of claim 1, further comprising:
water, ethylhexyl palmitate, *Butyrospermum parkii* butter, *Cocos nucifera* oil, cetearyl olivate, sorbitan oleate, stearyl alcohol, propanediol, glyceryl stearate, aloe barbadensis leaf juice, caprylhydroxamic acid, *alteromonas* ferment extract, glycosphingolipids, glycolipids, ferulic acid, retinyl palmitate, resveratrol, ergothioneine, *Linum usitatissimum* seed oil, *bacillus*/soybean ferment extract, tocopherol, sodium PCA, *Rosmarinus officinalis* leaf extract, and *Lavandula agustifolia*.

8. The skin care product of claim 7, wherein the skin care product is moisturizer.

9. The skin care product of claim 8, wherein the skin care product is configured to be applied to a user's face in the morning and in the evening to obtain a desired result.

10. The skin care product of claim 1, further comprising:
water, zinc oxide, *Brassica napus* extract, dimethicone, cyclopentasiloxane, caprylic triglyceride, propanediol, bentonite, cetearyl alcohol, montmorillonite, illite, sodium chloride, citric acid, Manuka honey, polyglyceryl-8 oleate, polyhydroxystearic acid, dimethicone/vinyl dimethicone crosspolymer, *bacillus*/soybean ferment extract, hyaluronic acid, dimethylmethoxy chromanyl palmitate, *Caesalpinia spinosa* fruit pod extract, *Helianthus annuus* sprout extract, maltodextrin, and lactic acid.

11. The skin care product of claim 10, wherein the skin care product is a sun protection product.

12. The skin care product of claim 11, wherein the skin care product is configured to be applied to a user's face in the morning to obtain a desired result.

* * * * *